(12) United States Patent
Lafay et al.

(10) Patent No.: US 7,476,691 B2
(45) Date of Patent: Jan. 13, 2009

(54) SULFAMATE BENZOTHIOPHENE DERIVATIVES AS STEROID SULFATASE INHIBITORS

(75) Inventors: Jean Lafay, Nice (FR); Benoît Rondot, La Colle sur Loup (FR); Denis Carniato, Marcoussis (FR); Paule Bonnet, Menton (FR); Thierry Clerc, La Turbie (FR); Jacqueline Shields, Nice (FR); Igor Duc, Cannes (FR); Eric Duranti, Saint Laurent du Var (FR)

(73) Assignee: Laboratoire Theramex (MC)

( * ) Notice: Subject to any disclaimer, the term of this patent is extended or adjusted under 35 U.S.C. 154(b) by 0 days.

(21) Appl. No.: 10/555,780

(22) PCT Filed: May 16, 2003

(86) PCT No.: PCT/EP03/08811

§ 371 (c)(1),
(2), (4) Date: Aug. 1, 2006

(87) PCT Pub. No.: WO2004/101545

PCT Pub. Date: Nov. 25, 2004

(65) Prior Publication Data

US 2007/0021492 A1    Jan. 25, 2007

(51) Int. Cl.
*A61K 31/381*    (2006.01)
*C07D 333/64*    (2006.01)
*C07D 333/66*    (2006.01)

(52) U.S. Cl. ............................. 514/446; 549/46; 549/53

(58) Field of Classification Search .................. 514/446; 549/46, 53
See application file for complete search history.

(56) References Cited

U.S. PATENT DOCUMENTS

2003/0008862 A1    1/2003    Li et al.

OTHER PUBLICATIONS

King, Med. Chem.: Principle and Practice (1994), p. 206-208.*
Woo et al, J. Med. Chem, 1998, 41, 1068-1083.

* cited by examiner

*Primary Examiner*—Taofiq A Solola
(74) *Attorney, Agent, or Firm*—Dennison, Schultz & MacDonald

(57) ABSTRACT

The present invention relates to sulfamate benzothiophene compounds of the formula: (I) wherein $R_1$, $R_2$, $R_3$, m and n are as defined in the specification. The invention also relates to pharmaceutical compositions containing these compounds and to methods of using them.

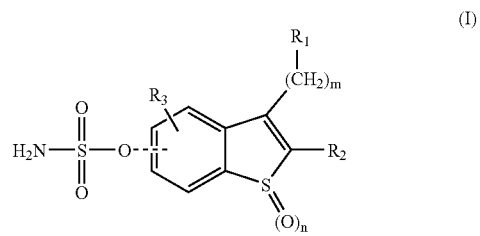

47 Claims, 1 Drawing Sheet

Formation of estrogens in humans

SULFAMATE BENZOTHIOPHENE DERIVATIVES AS STEROID SULFATASE INHIBITORS

This application is a filing under 35 USC 371 of PCT/EP2003/008811, May 16, 2003.

FIELD OF INVENTION

The present invention generally relates to steroid hormones, and more specifically relates to novel sulfamate benzothiophene derivatives which are inhibitors of the enzyme steroid sulfatase. The invention also relates to pharmaceutical compositions containing these derivatives, and to methods of using them.

BACKGROUND OF THE INVENTION

The enzyme steroid sulfatase (E.C. 3.1.6.2., STS) catalyses the hydrolysis of estrone sulfate to estrone and of DHEA sulfate to DHEA (Dibbelt L, Biol. Chem., Hoppe-Seyler, 1991, 372, 173-185 and Stein C, J. Biol. Chem., 1989, 264, 13865-13872).

The steroid sulfatase pathway has been the focus of recent interest in the context of breast cancer, with regard to the local intra-tissue formation of estrogens from the abundant circulating pool of estrone sulfate ($E_1S$) (Pasqualini J R, J. Steroid Biochem. Mol. Biol., 1999, 69, 287-292 and Purohit A, Mol. Cell. Endocrinol., 2001, 171, 129-135).

Inhibition of this enzyme would prevent $E_1S$ to yield free estrone ($E_1$), which in turn can be transformed into estradiol ($E_2$) by enzymatic reduction. In addition to the estrone sulfatase pathway, it is now believed that another potent estrogen, androstenediol (adiol) obtained from DHEA after hydrolysis of DHEA-S, could be another important route, in the support of growth and development of hormone dependent breast tumors.

The formation of estrogens in humans is schematically represented in FIG. 1.

In patients with hormone-dependent cancers, aromatase inhibitors are currently used to prevent estrogen synthesis. However, clinical trials showed a relative lack of efficacy for patients with estrogen receptors positive tumors (Castiglione-Gertsch M, Eur. J. Cancer, 1996, 32A, 393-395 and Jonat W, Eur. J. Cancer, 1996, 32A, 404-412). As an explanation, steroid sulfatase pathway could be another important route for estrogen formation in breast tumors.

EMATE (Ahmed S, Curr. Med. Chem., 2002, 9, 2, 263-273), estrone-3-sulfamate, is the historical standard steroid sulfatase inhibitor but with the major drawback of being estrogenic because of its mechanism of inhibition: the sulfamate moiety is cleaved during the process of enzyme inactivation, which releases $E_1$, not from $E_1S$ but from EMATE itself (Ahmed S, J. Steroid Biochem. Mol. Biol., 2002, 80, 429-440).

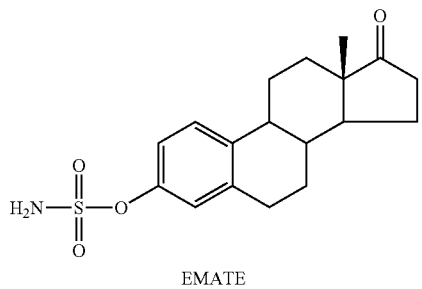

EMATE

Other non steroid sulfamate compounds which release derivatives without estrogenic properties are presented as acceptable drug candidates, in particular 6,6,7-COUMATE, a standard non-estrogenic sulfatase inhibitor from the literature (Purohit A, Cancer Res., 2000, 60, 3394-3396).

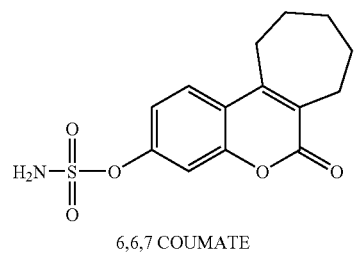

6,6,7 COUMATE

Accordingly, there is a need for steroid sulfatase inhibitors with the view of treating in particular estrogen-dependent diseases.

SUMMARY OF THE INVENTION

An object of this invention is to provide sulfamate benzothiophene derivatives which are potent steroid sulfatase inhibitors.

Another object of this invention is to provide a pharmaceutical composition containing, as active ingredient, a sulfamate benzothiophene derivative as mentioned above.

Still a further object of this invention is to provide the use of a sulfamate benzothiophene derivative in the manufacture of a medicament for treating or preventing various diseases and for managing reproductive functions in women, in men as well as in female and male wild or domestic animals.

In a first aspect of the invention there is provided a compound of formula (Ia) or formula (Ib):

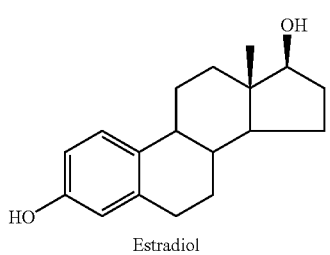

Estradiol

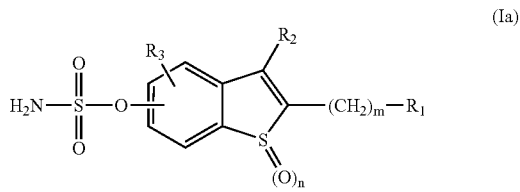

(Ia)

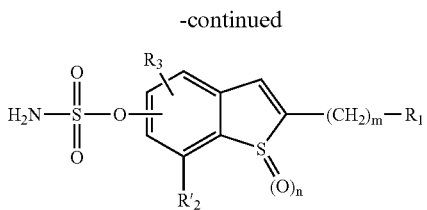

(Ib)

wherein:
R₁ is hydrogen, a $(C_1-C_6)$alkyl, a $(C_2-C_6)$alkene, a $(C_3-C_{12})$cycloalkyl or a $(C_3-C_{12})$cycloalkene wherein the cycloalkyl and the cycloalkene are optionally mono- or disubstituted with a $(C_1-C_4)$alkyl;
R₂ is hydrogen,
R'₂ is a $(C_1-C_6)$alkyl or a $(C_3-C_{12})$cycloalkyl;
R₃ is hydrogen, a $(C_1-C_6)$alkoxy or a halogen;
m is 0, 1, 2;
n is 0, 1, 2;
when m is 0, R₁ and R₂ can also form together a group —$(CH_2)_p$— in which p is 3, 4 or 5;
the dotted line indicates that the sulfamate group is in position 5- or 6- of the benzothiophene ring.

In another aspect of the invention there is provided a compound of formula (I):

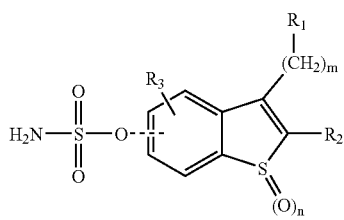

(I)

wherein:
R₁ is hydrogen;
R₂ is hydrogen, a $(C_1-C_6)$alkyl, or a $(C_3-C_{12})$cycloalkyl;
R₃ is hydrogen, a $(C_1-C_6)$alkoxy or a halogen;
m is 0;
n is 0, 1, 2;
the dotted line indicates that the sulfamate group is in position 5- or 6- of the benzothiophene ring.

In another aspect of the invention there is provided a compound of formula (I):

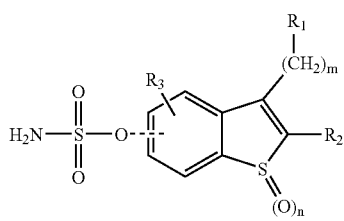

(I)

wherein:
R₁ and R₂ form together a group —$(CH_2)_p$— in which p is 3, 4 or 5;
R₃ is hydrogen, a $(C_1-C_6)$alkoxy or a halogen;
n is 0, 1, 2;

m is 0;
the dotted line indicates that the sulfamate group is in position 5- or 6- of the benzothiophene ring.

In some embodiments, the sulfamate benzothiophene derivatives of this invention can be represented by the following general formula (I):

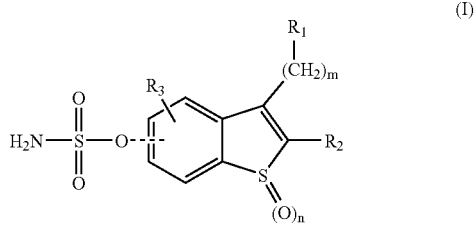

(I)

wherein:
R₁ is hydrogen, a $(C_1-C_6)$alkyl, a $(C_2-C_6)$alkene, a $(C_3-C_{12})$cycloalkyl or a $(C_3-C_{12})$cycloalkene, wherein the cycloalkyl and cycloalkene are optionally mono- or disubstituted with a $(C_1-C_4)$alkyl;
R₂ is hydrogen, a $(C_1-C_6)$alkyl or a $(C_3-C_{12})$cycloalkyl;
R₃ is hydrogen, a $(C_1-C_6)$alkoxy or a halogen;
m is 0, 1, 2;
n is 0, 1, 2;
when m is 0, R₁ and R₂ can also form together a group —$(CH_2)_p$— in which p is 3, 4 or 5;
the dotted line indicates that the sulfamate group ($OSO_2(NH_2)$) is in position 5- or 6- of the benzothiophene ring.

Among the compounds of formula (I), those fulfilling at least one of the following conditions, are particularly preferred:
R₁ is hydrogen, a $(C_1-C_6)$ alkyl or a $(C_3-C_{12})$cycloalkyl optionally mono- or disubstituted with a $(C_1-C_4)$alkyl, preferably R₁ is a $(C_3-C_{10})$cycloalkyl optionally mono- or disubstituted with a $(C_1-C_4)$alkyl;
m is 0 or 1;
R₂ is hydrogen;
R₃ is hydrogen;
n is 0 or 2;
the sulfamate group is in position 6- of the benzothiophene group.

In the description and appended claims, a $(C_1-C_4)$ or $(C_1-C_6)$alkyl is understood as meaning a linear or branched saturated hydrocarbon chain having 1 to 4 or, respectively, 1 to 6 carbon atoms. Such an alkyl radical is for example a methyl, ethyl, propyl, isopropyl, butyl, isobutyl, tert-butyl, pentyl, isopentyl or hexyl radical.

A $(C_1-C_6)$alkoxy is understood as meaning a group —OR in which R is a $(C_1-C_6)$alkyl as defined above.

A $(C_3-C_{12})$cycloalkyl is understood as meaning a saturated mono- or bicyclic hydrocarbon having 3 to 12 carbon atoms. A $(C_3-C_{12})$cycloalkyl radical is for example a cyclopropyl, cyclobutyl, cyclopentyl, cyclohexyl, cycloheptyl, cyclooctyl, cyclodecyl or adamantyl radical.

A halogen is understood as meaning a chlorine, bromine, fluorine or iodine atom.

A $(C_2-C_6)$alkene is understood as meaning a linear or branched unsaturated hydrocarbon chain having 2 to 6 carbon atoms. A $(C_2-C_6)$alkene radical is for example an ethylene or a propene, butene, pentene or hexene radical.

A $(C_3-C_{12})$cycloalkene is understood as meaning an unsaturated mono- or bicyclic hydrocarbon having 3 to 12 carbon atoms. A $(C_3-C_{12})$cycloalkene radical is for example a cyclopropene, cyclobutene, cyclopentene, cyclohexene, cyclooctene, cyclodecene or adamantene radical.

In view of their capability to inhibit steroid sulfatase, and thus to dry out other sources of endogenous estrogens as compared with aromatase inhibitors, the compounds of the present invention can be used alone or in combination with one or several other sexual endocrine therapeutic agents such as antiestrogens, SERMs (Selective Estrogen Receptor Modulators), antiaromatases, antiandrogens, lyase inhibitors, progestins or LH-RH agonists or antagonists, in the treatment or prevention of estrogen-dependent disorders or diseases. The compounds of the invention can also be used for the control or management of estrogen-regulated reproductive functions such as male or female fertility, pregnancy, abortion or delivery in humans as well as in wild or domestic animal species, alone or in combination with one or several other therapeutic agents such as LH-RH agonists or antagonists, estroprogestative contraceptives, progestins, antiprogestins or prostaglandins.

The breasts being sensitive targets of estrogen-stimulated proliferation and/or differentiation, the compounds of the invention can be used in the treatment or prevention of benign breast diseases in women, gynecomastia in men and in benign or malignant breast tumors with or without metastasis both in men and women or in male or female domestic animals. The compounds of the invention can also be used in the treatment or prevention of benign or malignant diseases of the uterus or the ovary. In each case, the compounds of the invention can be used alone or in combination with one or several other sexual endocrine therapeutic agents such as those mentioned above.

As the enzyme steroid sulfatase transforms DHEA sulfate into DHEA, a precursor of active androgens (testosterone and dihydrotestosterone), the compounds of the invention can be used in the treatment or prevention of androgen-dependent diseases such as androgenic alopecia (male pattern loss) (Hoffman R et al., J. Invest. Dermatol., 2001, 117, 1342-1348) or acne (Billich A et al., 1999, WO 9952890), benign or malignant diseases of the prostate or the testis (Reed M J, Rev. Endocr. Relat. Cancer, 1993, 45, 51-62), alone or in combination with one or several other sexual endocrine therapeutic agents, such as antiandrogens, antiestrogens, SERMs, antiaromatase, progestins, lyase inhibitors or LH-RH agonists or antagonists.

Inhibitors of steroid sulfatase are also potentially involved in the treatment of cognitive dysfunction, because they are able to enhance learning and spatial memory in the rat (Johnson DA, Brain Res, 2000, 865, 286-290). DHEA sulfate as a neurosteroid affects a number of neurotransmitter systems, including those involving acetylcholine, glutamate, and GABA, resulting in increased neuronal excitability (Wolf O T, Brain Res. Rev, 1999, 30, 264-288).

In addition, estrogens are involved in the regulation of the balance between $Th_1$ and $Th_2$ predominant immune functions and may therefore be useful in the treatment or prevention of gender-dependent auto-immune diseases such as lupus, multiple sclerosis, rheumatoid arthritis and the like (Daynes R A, J. Exp. Med, 1990, 171, 979-996). Steroid sulfatase inhibition was shown to be protective in models of contact allergy and collagen-induced arthritis in rodents (Suitters A J, Immunology, 1997, 91, 314-321).

Studies using 2-MeOEMATE have shown that steroid sulfatase inhibitors have potent estradiol-independent growth-inhibitory effect (MacCARTHY-MOOROGH L, Cancer Research, 2000, 60, 5441-5450). A decrease in tumor volume was surprisingly observed with the compounds of the invention, with low tumor steroid sulfatase inhibition. In view of this, the compounds of the invention could lead to a decrease in cellular division because of the large interaction between such new chemical entities and the microtubular network within the cancerous cell, whatever the tissue, including breast, endometrium, uteri, prostate, testis or metastasis generated from. The compounds of the invention could therefore be useful in the treatment of non-estrogeno-dependent cancer.

Accordingly, it is another object of the invention to provide a method for treating the above-mentioned diseases or disorders, in particular estrogen-dependent diseases or disorders, i.e. estrogen-induced or estrogen-stimulated diseases or disorders (GOLOB T, Bioorg. Med. Chem., 2002, 10, 3941-3953). The method comprises administering to a subject (human or animal) in need thereof a therapeutically effective amount of a compound of formula (I).

The pharmaceutical compositions containing the active ingredient(s) may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient(s) in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. The tablets may also be coated by the technique described in U.S. Pat. No. 4,256,108; 4,166,452 or 4,265,874 to form osmotic therapeutic tablets for control release.

Formulations for oral use may also be presented as hard gelatin capsules wherein the active ingredient(s) is (are) mixed with an inert solid diluent, for example, calcium carbonate, calcium phosphate, or kaolin, or as soft gelatin capsules wherein the active ingredient(s) is (are) mixed with water or an oil medium, for example peanut oil, liquid paraffin, or olive oil.

Aqueous suspensions contain the active ingredient(s) in admixture with excipients suitable for the manufacture of aqueous suspensions. Such excipients are suspending agents, for example sodium carboxymethylcellulose, methylcellulose, hydroxy-propylmethylcellulose, sodium alginate, polyvinylpyrrolidone, gum tragacanth and gum acacia; dispersing or wetting agents such as a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient(s) in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those mentioned above, and flavouring agents may be added to provide a palatable oral preparation. These compositions may be preserved by the addition of an anti-oxidant such as ascorbic acid.

Dispersible powders and granules suitable for the preparation of an aqueous suspension by the addition of water provide the active ingredient(s) in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present. The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

The pharmaceutical compositions of the invention may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed, water, Ringer's solution and isotonic sodium chloride solution can be mentioned. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the invention can be used in the treatment of the above-indicated diseases or disorders at dosage levels of the order of from about 0.0001 mg to about 10 mg/kg of body weight per day, or alternatively from about 0.01 mg to about 100 mg per patient per day.

The amount of active ingredient(s) that may be combined with the carrier materials to produce a single dosage form will vary depending upon the host treated and the particular mode of administration.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The sulfamate benzothiophene derivatives of formulas (I), (Ia) and (Ib) can be prepared according to the following general scheme 1.

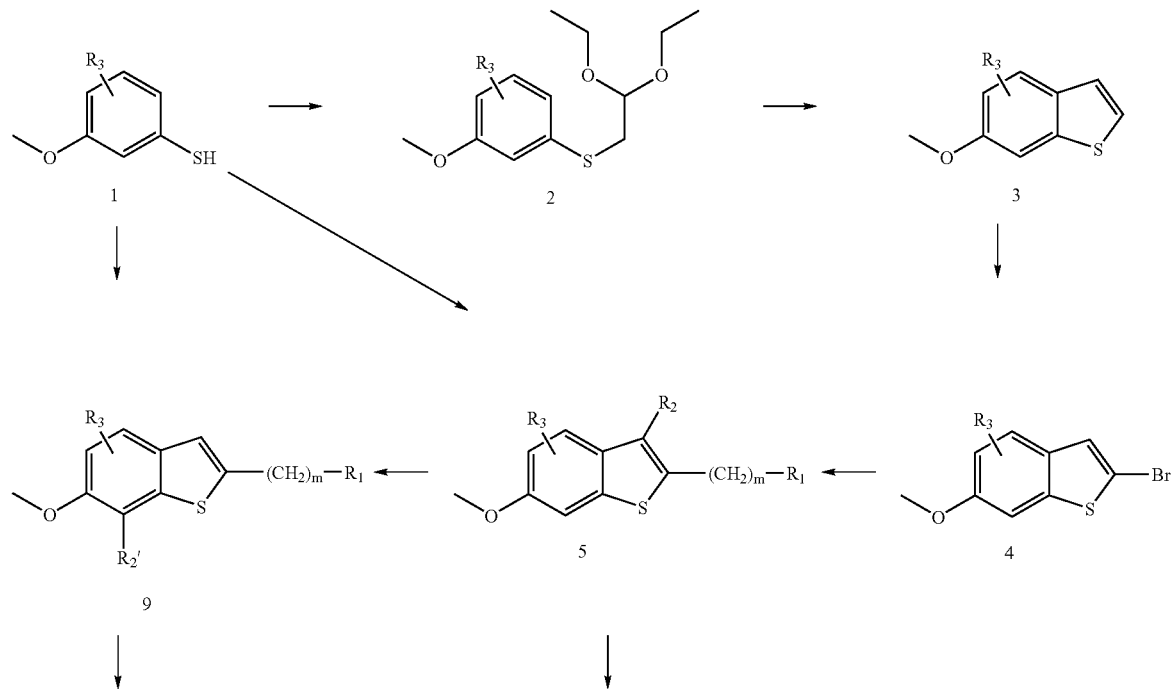

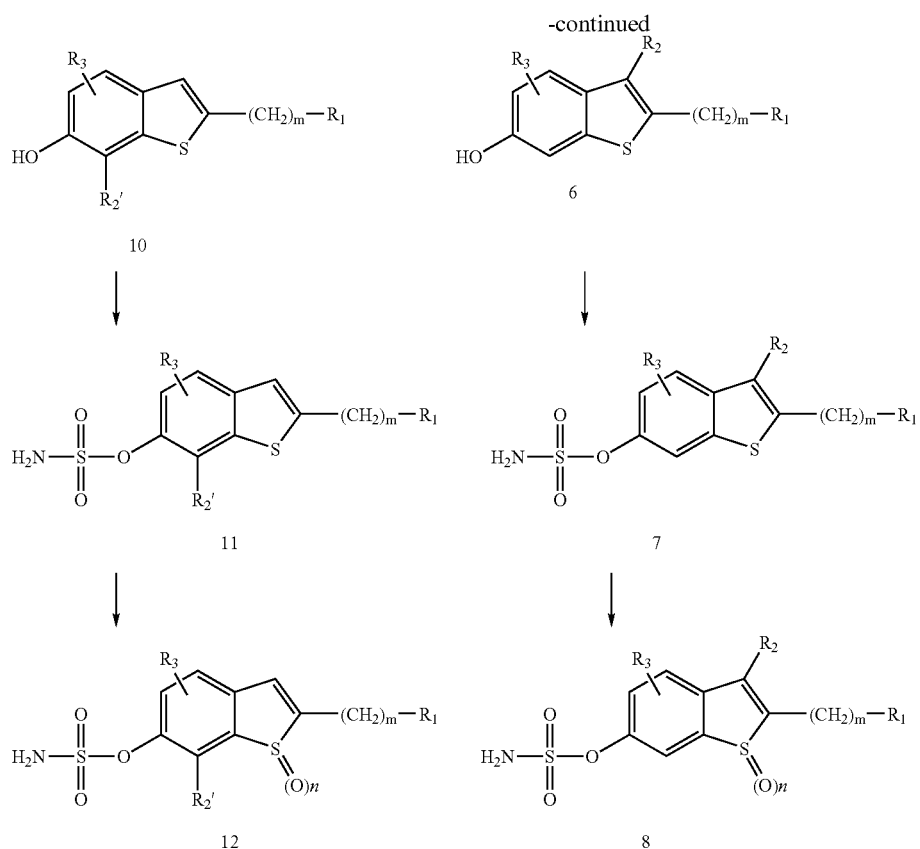

According to scheme 1 the 3-methoxythiophenol (1) is condensed with 2-bromo-1,1-diethoxyethane and the thio-compound intermediate (2) is cyclised with different acids: polyphosphoric acid (Bioor. Med. Chem. Lett, 1999, 9, 759-64) or methanesulfonic acid to afford the 6-methoxy-benzothiophene (3). This compound can also be prepared by reaction of a Lewis acid, trifluoroborane, with compound (2) using the conditions described by S. Graham (J. Med. Chem., 1989, 32, 2548-54).

The 6-methoxy-benzothiophene (3) is converted to the bromo derivative (4) with N-bromosuccinimid and APTS using the conditions described by Y. Fort (Tetrahedron. 1994, 50, 11893-902). (4) is transformed into an organomagnesium bromide, and then condensed with a ketone or an aldehyde to afford the monosubstituted benzothiophene (5) using standard conditions.

The disubstituted benzothiophene (9) can be prepared by alkylation of the monosubstituted compound (5) using the conditions described by Kano. S (Heterocycles, 1982, 19, 6, 1033-37).

The compounds where $R_1$ and $R_2$ form together a group —$(CH_2)_p$—, such as the 7-methoxy-1,2,3,4-tetrahydrodibenzothiophene (p=4), can be prepared using the conditions described by Oliveira. M (Tetrahedron, 2002, 58, 1709-18).

Deprotection of the methoxybenzothiophene monosubstituted (5) or disubstituted (9) with tribromoborane gave the hydroxy compounds (6) and (10) prepared using the conditions described by McOmie. J. F. W (Tetrahedron, 1968, 24, 2289-92). These compounds were transformed into the corresponding sulfamates (7) and (11) by treatment with sodium hydride, with amidochlorosulfonic acid (Nussbaumer. P, J Med Chem, 2002, 45, 4310-20), or by reaction with sulfamoyl chloride in dimethylacetamide (DMAc) (Makoto. O, Tetrahedron letters, 2000, 41, 7047-51).

Oxidation of (7) and (11) by hydrogen peroxide in trifluoroacetic acid, following the conditions described by GRIVAS S, and RONNE E. (Acta Chemica Scandinavia, 1995, 49, 225-229), gave the final benzothiophenes (8) and (12).

The compounds of formula (I) where the sulfamate group is in position 5- of the benzothiophene ring can be prepared in the same way but starting from 4-methoxythiophenol.

The following examples are intended to illustrate and not to limit the scope of the invention.

Figure 1:
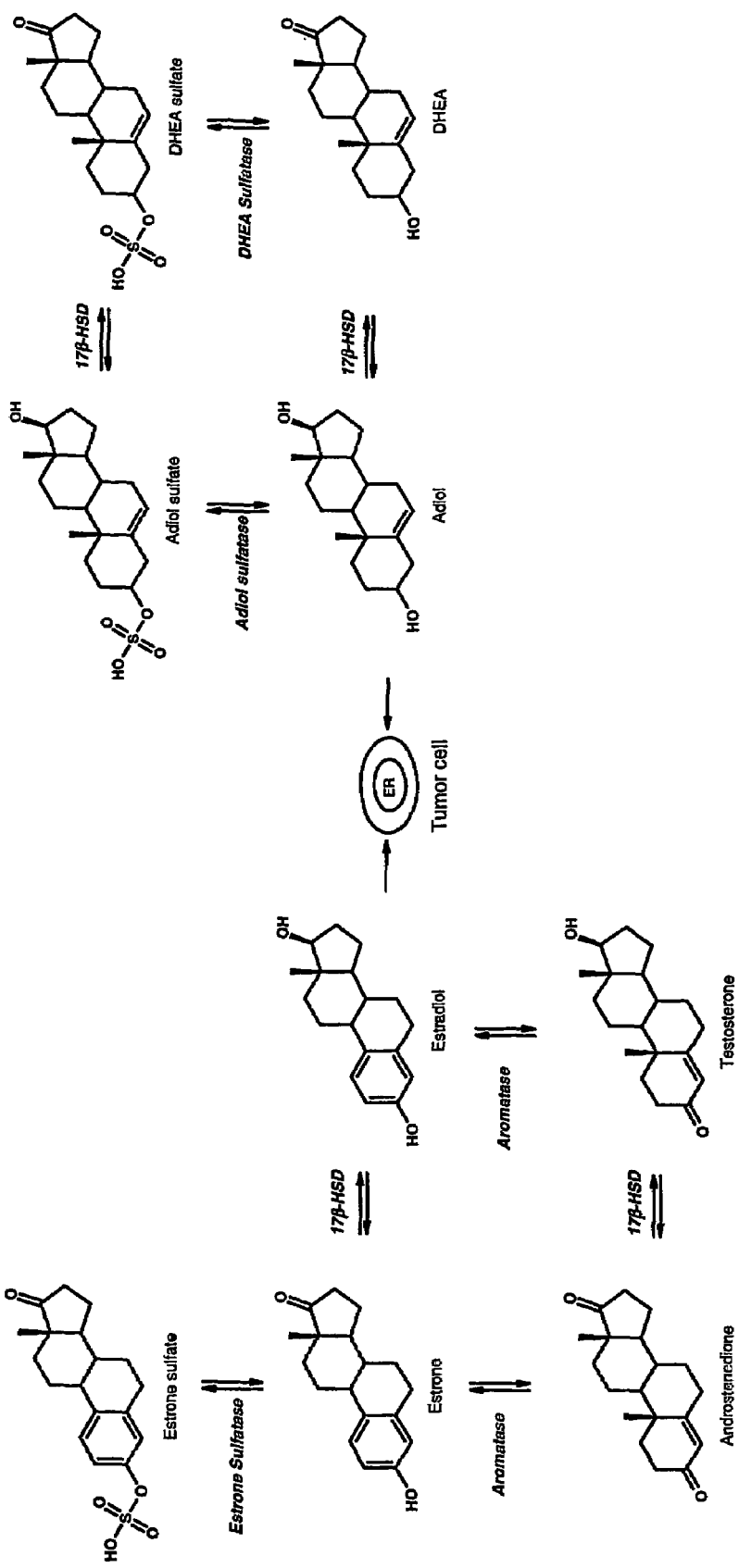
FIG. 1 is a schematic representation of the production of estrogen in humans.

PREPARATION OF THE
3-BROMO-6-METHOXYBENZOTHIOPHENE (4)

Example 1

6-Methoxybenzothiophene (3)

Bromoacetaldehyde diethyl acetal (16.50 ml, 0.11 mol) was added dropwise to a mixture of m-methoxybenzenethiol (1) (15 ml, 0.12 mol) and $K_2CO_3$ (16.60 g, 0.12 mol) in acetone (150 ml) at room temperature. The reaction mixture was stirred for 16 h and then filtered. The solid was washed with acetone, and the combined filtrates were concentrated under vacuum. The residue was diluted with water and extracted with Et$_2$O. The organic phase was washed with 0.5 M KOH, water, and brine, dried over Na$_2$SO$_4$, filtered, and concentrated under vacuum to give 27.40 g of compound (2) as a dark yellow oil.

$^1$H-NMR (CDCl$_3$): 1.18 (t, 6H), 3.13 (d, 2H), 3.43-3.73 (m, 4H), 3.77 (s, 3H), 4.67 (t, 1H), 6.60-7.27 (m, 4H).

A solution of (2) (13.00 g, 0.051 mol) in CH$_2$Cl$_2$ (100 ml) was added dropwise to a solution of BF$_3$.Et$_2$O (6.70 ml, 0.054 mol) in CH$_2$Cl$_2$ (1000 ml) at room temperature under nitrogen atmosphere. After hydrolysis, the reaction mixture was stirred until both phases became clear. The CH$_2$Cl$_2$ layer was separated, and the aqueous layer was extracted with CH$_2$Cl$_2$. The combined organic phases were dried over Na$_2$SO$_4$, filtered, and concentrated under vacuum to give 8.68 g of a 1:10 mixture of 4 and 6-methoxybenzothiophene (3) as a dark brown oil. The crude product was used without purification.

Major isomer (3) $^1$H-NMR (CDCl$_3$): 3.85 (s, 3H), 6.98 (dd, 1H), 7.23 (s, 2H), 7.35 (d, 1H), 7.68 (d, 1H).

Example 2

2-Bromo-6-methoxybenzothiophene (4)

N-bromosuccinimide (14.70 g, 82.59 mmol) and p-toluenesulfonic acid (2.70 g, 15.68 mmol) were added to a solution of benzothiophene (3) (15.10 g, 92.07 mmol) in 1,2-dichloroethane (300 ml). The mixture was maintained at 70° C. for 35 min, cooled in an ice bath, and the succinimide was removed by filtration. The solution was extracted with saturated sodium bicarbonate solution, dried over Na$_2$SO$_4$, filtered, and concentrated under vacuum to give 22.00 g as an oil. Crystallisation from pentane afforded a white solid (16.50 g, 74%), mp 62° C.

$^1$H-NMR (CDCl$_3$): 3.85 (s, 3H), 6.9 (dd, 1H), 7.50 (m, 2H), 7.65 (d, 1H)

PREPARATION OF MONOSUBSTITUTED BENZOTHIOPHENE (5)

Example 3

2-Cyclohexyl-6-methoxybenzothiophene

To Mg (0.22 g, 9.05 mmol) under argon in Et$_2$O (20 ml) was added dropwise a solution of bromide (4) (2.00 g, 8.23 mmol) in Et$_2$O (20 ml). The mixture was refluxed for 2 h, a solution of cyclohexanone (1.00 ml, 9.87 mmol) in Et$_2$O (5 ml) was added and the mixture was refluxed for 2 h. It was poured into iced water. The solution was extracted with ethyl acetate, dried over Na$_2$SO$_4$, filtered, and concentrated under vacuum to give 8.00 g as an oil. Triturating from diisopropyl ether afforded 2-(1-hydroxycyclohexyl)-6-methoxybenzothiophene as a white powder (0.90 g, 65%).

$^1$H-NMR (DMSOd$_6$): 1.20-2.00 (m, 10H), 3.80 (s, 3H), 5.30 (s, 1H), 6.93 (dd, 1H), 7.10 (s, 1H), 7.42 (d, 1H), 7.60 (d, 1H).

To 2-(1-hydroxycyclohexyl)-6-methoxybenzothiophene (0.30 g, 1.14 mmol) under argon in dichloromethane (10 ml) was added dropwise triethylsilane (0.22 ml, 1.37 mmol). Then, the solution was stirred at 0° C., and trifluoroacetic acid (5.00 ml, 67.31 mmol) was added. After 2 h at room temperature the mixture was poured into saturated aqueous NaHCO$_3$ and ice, extracted with ethyl acetate, dried over Na$_2$SO$_4$, filtered, and concentrated under vacuum to give 0.30 g as an oil (100%). Crystallisation from diisopropyl ether afforded a white crystal (0.20 g, 70%).

$^1$H-NMR (DMSOd$_6$): 1.00-2.20 (m, 11H), 2.72 (m, 1H), 3.75 (s, 3H), 6.93 (dd, 1H), 7.01 (s, 1H), 7.43 (d, 1H), 7.58 (d, 1H).

Using the same procedure but replacing cyclohexanone by:
cyclopentanone
cycloheptanone
cyclooctanone
cyclodecanone
4-methylcyclohexanone
2-methylcyclohexanone
2,2-dimethylcyclopentanone
2-adamantanone
propanal
hexanal
cyclohexanecarboxaldehyde
cycloheptanecarboxaldehyde (prepared following J. G. Traynham et al, Tetrahedron, 7, 1959, 165-72), To Mg (0.22 g, 9.05 mmol) under argon in Et$_2$O (20 ml) was added dropwise a solution of bromide (4) (2.00 g, 8.23 mmol) in Et$_2$O (20 ml). The mixture was refluxed for 2 h, a solution of cyclohexanone (1.00 ml, 9.87 mmol) in Et$_2$O (5 ml) was added and the mixture was refluxed for 2 h. It was poured into iced water. The solution was extracted with ethyl acetate, dried over Na$_2$SO$_4$, filtered, and concentrated under vacuum to give 8.00 g as an oil. Triturating from diisopropyl ether afforded 2-(1-hydroxycyclohexyl)-6-methoxybenzothiophene as a white powder (0.90 g, 65%).

$^1$H-NMR (DMSOd$_6$): 1.20-2.00 (m, 10H), 3.80 (s, 3H), 5.30 (s, 1H), 6.93 (dd, 1H), 7.10 (s, 11H), 7.42 (d, 1H), 7.60 (d, 1H).

To 2-(1-hydroxycyclohexyl)-6-methoxybenzothiophene (0.30 g, 1.14 mmol) under argon in dichloromethane (10 ml) was added dropwise triethylsilane (0.22 ml, 1.37 mmol). Then, the solution was stirred at 0° C., and trifluoroacetic acid (5.00 ml, 67.31 mmol) was added. After 2 h at room temperature the mixture was poured into saturated aqueous NaHCO$_3$ and ice, extracted with ethyl acetate, dried over Na$_2$SO$_4$, filtered, and concentrated under vacuum to give 0.30 g as an oil (100%). Crystallisation from diisopropyl ether afforded a white crystal (0.20 g, 70%).

$^1$H-NMR (DMSOd$_6$): 1.00-2.20 (m, 11H), 2.72 (m, 1H), 3.75 (s, 3H), 6.93 (dd, 11H), 7.01 (s, 1H), 7.43 (d, 1H), 7.58 (d, 1H).

Using the same procedure but replacing cyclohexanone by:
cyclopentanone
cycloheptanone
cyclooctanone
cyclodecanone
4-methylcyclohexanone
2-methylcyclohexanone
2,2-dimethylcyclopentanone
2-adamantanone
propanone
hexanone
cyclohexanecarboxaldehyde
cycloheptanecarboxaldehyde (prepared following J. G. Traynham et al, Tetrahedron, 7, 1959, 165-72), the following compounds were respectively obtained:

Example 4

2-cyclopentyl-6-methoxybenzothiophene $^1$H-NMR (DMSOd$_6$): 1.40-2.20 (m, 8H), 2.72 (m, 1H), 3.80 (s, 3H), 6.94 (dd, 1H), 7.13 (s, 1H), 7.45 (d, 1H), 7.64 (d, 1H).

Example 5

2-cycloheptyl-6-methoxybenzothiophene $^1$H-NMR (DMSOd$_6$): 1.40-2.20 (m, 12H), 3.05 (m, 1H), 3.80 (s, 3H), 6.90 (dd, 1H), 7.00 (s, 1H), 7.41 (d, 1H), 7.57 (d, 1H).

Example 6

2-cyclooctyl-6-methoxybenzothiophene $^1$H-NMR (DMSOd$_6$): 1.20-2.15 (m, 14H), 3.10 (m, 11H), 3.77 (s, 3H), 6.92 (dd, 1H), 7.01 (s, 1H), 7.41 (d, 1H), 7.58 (d, 1H).

Example 7

2-cyclodecyl-6-methoxybenzothiophene $^1$H-NMR (DMSOd$_6$): 1.20-2.15 (m, 18H), 3.12 (m, 1H), 3.75 (s, 3H), 6.92 (dd, 1H), 7.01 (s, 1H), 7.40 (d, 1H), 7.55 (d, 1H).

Example 8

2-(4-methylcyclohexyl)-6-methoxybenzothiophene $^1$H-NMR (DMSOd$_6$): 0.70-2.15 (m, 12H), 2.72 (m, 0.5H, diastereoisomer), 2.99 (m, 0.5H, diastereoisomer), 3.76 (s, 3H), 6.92 (dd, 1H), 7.02 (s, 1H), 7.41 (d, 1H), 7.58 (d, 1H).

Example 9

2-(2-methylcyclohexyl)-6-methoxybenzothiophene $^1$H-NMR (DMSOd$_6$): 0.70-2.20 (m, 12H), 2.70 (m, 0.5H, diastereoisomer), 3.02 (m, 0.5H, diastereoisomer), 3.75 (s, 3H), 6.92 (dd, 1H), 7.02 (s, 1H), 7.40 (d, 1H), 7.55 (d, 1H).

Example 10

2-(2,2-dimethylcyclopentyl)-6-methoxybenzothiophene $^1$H-NMR (DMSOd$_6$): 0.70 (s, 3H), 1.10 (s, 3H), 1.45-2.20 (m, 6H), 2.93 (m, 1H), 3.78 (s, 3H), 7.02 (dd, 1H), 7.04 (s, 1H), 7.43 (d, 11H), 7.60 (d, 1H).

Example 11

2-(2-adamantyl)-6-methoxybenzothiophene $^1$H-NMR (DMSOd$_6$): 1.40-2.40 (m, 14H), 3.19 (br s, 1H), 3.79 (s, 3H), 6.92 (dd, 1H), 7.08 (s, 1H), 7.43 (d, 1H), 7.60 (d, 1H).

Example 12

2-propyl-6-methoxybenzothiophene $^1$H-NMR (DMSOd$_6$): 0.95 (t, 3H), 1.68 (m, 2H), 2.78 (t, 2H), 3.79 (s, 3H), 6.92 (dd, 1H), 7.00 (s, 1H), 7.43 (d, 1H), 7.58 (d, 1H).

Example 13

2-hexyl-6-methoxybenzothiophene $^1$H-NMR (DMSOd$_6$): 0.85 (t, 3H), 1.10-1.80 (m, 8H), 2.82 (t, 2H), 3.79 (s, 3H), 6.92 (dd, 1H), 7.01 (s, 1H), 7.45 (d, 1H), 7.58 (d, 1H).

Example 14

2-cyclohexylmethyl-6-methoxybenzothiophene $^1$H-NMR (DMSOd$_6$): 0.75-1.85 (m, 11H), 2.70 (d, 2H), 3.80 (s, 3H), 6.92 (dd, 1H), 7.00 (s, 1H), 7.42 (d, 1H), 7.59 (d, 1H).

Example 15

2-cycloheptylmethyl-6-methoxybenzothiophene
1'-NMR (DMSOd$_6$): 1.00-1.90 (m, 13H), 2.71 (d, 2H), 3.80 (s, 3H), 6.93 (dd, 1H), 7.00 (s, 1H), 7.42 (d, 1H), 7.59 (d, 1H).

PREPARATION OF MONOSUBSTITUTED BENZOTHIOPHENOL (6)

Example 16

2-Cyclohexyl-benzothiophene-6-ol

A solution of 2-cyclohexyl-6-methoxybenzothiophene (4.00 g, 16.0 mmol) in 40 ml of dichloromethane is added at room temperature to a solution of boron tribromide (24 ml, 24 mmol). After 2 h at room temperature the mixture was hydrolysed with saturated aqueous NaHCO$_3$, extracted with dichloromethane, dried over Na$_2$SO$_4$, filtered, and concentrated in vacuum to give the alcohol (3.60 g as an oil, 97%).

$^1$H-NMR (CDCl$_3$): 1.10-2.10 (m, 10H), 2.80 (m, 1H), 6.78 (dd, 1H), 6.94 (s, 1H), 7.17 (d, 1H), 7.48 (d, 1H), 9.42 (s, 1H, OH).

Using the same procedure but replacing 3-cyclohexyl-6-methoxybenzothiophene by:
  2-cyclopentyl-6-methoxybenzothiophene
  2-cycloheptyl-6-inethoxybenzothiophene
  2-cyclooctyl-6-methoxybenzothiophene
  2-cyclodecyl-6-methoxybenzothiophene
  2-(4-methylcyclohexyl)-6-methoxybenzothiophene
  2-(2-methylcyclohexyl)-6-methoxybenzothiophene
  2-(2,2-dimethylcyclopentyl)-6-methoxybenzothiophene
  2-(2-adamantyl)-6-methoxybenzothiophene
  2-propyl-6-methoxybenzothiophene
  2-hexyl-6-methoxybenzothiophene
  2-cyclohexylmethyl-6-methoxybenzothiophene
  2-cycloheptylmethyl-6-methoxybenzothiophene, the following compounds were respectively obtained:

Example 17

2-cyclopentyl-benzothiophene-6-ol mp 116° C.

$^1$H-NMR (DMSOd$_6$): 1.45-2.20 (m, 8H), 3.25 (m, 1H), 6.78 (dd, 1H), 6.96 (s, 1H), 7.15 (d, 1H), 7.47 (d, 1H), 9,45 (s, 1H, OH).

Example 18

2-cycloheptyl-benzothiophene-6-ol mp 140° C.
$^1$H-NMR (DMSOd$_6$): 1.35-2.15 (m, 12H), 3.00 (m, 1H), 6.79 (dd, 1H), 6.94 (s, 1H), 7.17 (d, 1H), 7.48 (d, 1H), 9,45 (s, 1H, OH).

Example 19

2-cyclooctyl-benzothiophene-6-ol mp 100° C.
$^1$H-NMR (DMSOd$_6$): 1.35-2.10 (m, 14H), 3.07 (m, 1H), 6.78 (dd, 1H), 6.95 (s, 1H), 7.15 (d, 1H), 7.47 (d, 1H), 9,42 (s, 1H, OH).

Example 20

2-cyclodecyl-benzothiophene-6-ol mp 108° C.
$^1$H-NMR (DMSOd$_6$): 1.30-2.10 (m, 18H), 3.22 (m, 1H), 6.79 (dd, 1H), 6.99 (s, 1H), 7.15 (d, 1H), 7.48 (d, 1H), 9,42 (s, 1H, OH).

Example 21

2-(4-methylcyclohexyl)-benzothiophene-6-ol mp 132° C.
$^1$H-NMR (DMSOd$_6$): 0.70-2.10 (m, 12H), 2.70 (m, 1H), 6.80 (dd, 1H), 6.92 (s, 1H), 7.15 (d, 1H), 7.48 (d, 1H), 9,42 (s, 1H, OH).

Example 22

2-(2-methylcyclohexyl)-benzothiophene-6-ol mp 125° C.
$^1$H-NMR (DMSOd$_6$): 0.60-2.20 (m, 12H), 3.05 (m, 1H), 6.80 (dd, 1H), 6.90 (s, 1H), 7.16 (d, 1H), 7.50 (d, 1H), 9,45 (s, 1H, OH).

Example 23

2-(2,2-dimethylcyclopentyl)-benzothiophene-6-ol mp 90° C.
$^1$H-NMR (DMSOd$_6$): 0.70 (s, 3H), 1.09 (s, 3H), 1.45-2.20 (m, 6H), 2.92 (dd, 1H), 6.80 (dd, 1H), 6.99 (s, 1H), 7.17 (d, 1H), 7.51 (d, 1H), 9.45 (s, 1H, OH).

Example 24

2-(2-adamantyl)-benzothiophene-6-ol mp 184° C.
$^1$H-NMR (DMSOd$_6$): 1.40-2.40 (m, 14H), 3.16 (br s, 1H), 6.80 (dd, 1H), 7.00 (s, 1H), 7.17 (d, 1H), 7.50 (d, 1H), 9,43 (s, 1H, OH).

Example 25

2-propyl-benzothiophene-6-ol mp 56° C.
$^1$H-NMR (DMSOd$_6$): 0.97 (t, 3H), 1.68 (m, 2H), 2.79 (t, 2H), 6.80 (dd, 1H), 6.96 (s, 1H), 7.17 (d, 1H), 7.50 (d, 1H), 9.46 (s, 1H, OH).

Example 26

2-hexyl-benzothiophene-6-ol mp 68° C.
$^1$H-NMR (DMSOd$_6$): 0.85 (t, 3H), 1.10-1.80 (m, 8H), 2.78 (t, 2H), 6.79 (dd, 11H), 6.95 (s, 1H), 7.16 (d, 11H), 7.48 (d, 11H), 9.45 (s, 11H, OH).

Example 27

2-cyclohexylmethyl-benzothiophene-6-ol mp 97° C.
$^1$H-NMR (DMSOd$_6$): 0.75-1.80 (m, 11H), 2.68 (d, 2H), 6.78 (dd, 11H), 6.91 (s, 1H), 7.16 (d, 1H), 7.49 (d, 1H), 9.45 (s, 1H, OH).

Example 28

2-cycloheptylmethyl-benzothiophene-6-ol mp 82° C.
$^1$H-NMR (DMSOd$_6$): 1.00-1.90 (m, 13H), 2.72 (d, 2H), 6.80 (dd, 11H), 6.92 (s, 11H), 7.18 (d, 1H), 7.49 (s, 1H), 9.48 (s, 1H, OH).

PREPARATION OF SULFAMIC ACID MONOSUBSTITUTED BENZOTHIOPHENYL ESTER (7)

Example 29

Sulfamic acid, 2-cyclohexyl-benzothiophene-6-yl ester

Sodium hydride (0.60 g, 24.8 mmol) was carefully added to a solution of 2-cyclohexyl-benzothiophene-6-ol (3.60 g, 15.50 mmol) in dry DMF (36 ml) at 0° C. After being stirred for 30 min at room temperature and 30 min at 50° C., the mixture was cooled (ice/water) and amidochlorosulfonic acid (4.45 g, 38.00 mmol) was added. After 3 h at room temperature the mixture was hydrolysed with saturated aqueous NH$_4$Cl, extracted with ethyl acetate, dried over Na$_2$SO$_4$, filtered, and concentrated under vacuum to give the crude product (4.80 g as oil). Flash chromatography on silica gel (toluene/1,4-dioxan: 8/2) yielded a limpid oil which was crystallised from ethanol to give the title product (0.50 g, 10%, mp 128° C.).

$^1$H-NMR (CDCl$_3$): 1.15-2.20 (m, 10H), 2.90 (m, 1H), 7.18 (s, 1H), 7.24 (dd, 1H), 7.30 (d, 1H), 7.32 (s, 1H), 7.98 (s, 2H, NH$_2$).

Using the same procedure but replacing 3-cyclohexylbenzothiophene-6-ol by:
- 2-cyclopentyl-benzothiophene-6-ol
- 2-cycloheptyl-benzothiophene-6-ol
- 2-cyclooctyl-benzothiophene-6-ol
- 2-cyclodecyl-benzothiophene-6-ol
- 2-(4-methylcyclohexyl)-benzothiophene-6-ol
- 2-(2-methylcyclohexyl)-benzothiophene-6-ol
- 2-(2,2-dimethylcyclopentyl)-benzothiophene-6-ol
- 2-(2-adamantyl)-benzothiophene-6-ol
- 2-propyl-benzothiophene-6-ol
- 2-hexyl-benzothiophene-6-ol
- 2-cyclohexylmethyl-benzothiophene-6-ol
- 2-cycloheptylmethyl-benzothiophene-6-ol, the following compounds were respectively obtained:

Example 30

Sulfamic acid, 2-cyclopentyl-benzothiophene-6-yl ester mp 110° C.
$^1$H-NMR (DMSOd$_6$): 1.50-2.30 (m, 8H), 3.39 (m, 1H), 7.20 (s, 1H), 7.72 (dd, 1H), 7.78 (d, 1H), 7.95 (s, 2H, NH$_2$).

Example 31

Sulfamic acid, 2-cycloheptyl-benzothiophene-6-yl ester mp 132° C.
$^1$H-NMR (DMSOd$_6$): 1.35-2.20 (m, 12H), 3.12 (m, 1H), 7.19 (s, 1H), 7.24 (dd, 1H), 7.75 (d, 1H), 7.80 (d, 1H), 7.95 (s, 2H, NH$_2$).

Example 32

Sulfamic acid, 2-cyclooctyl-benzothiophene-6-yl ester mp 126° C.
$^1$H-NMR (DMSOd$_6$): 0.90-2.20 (m, 14H), 3.18 (m, 1H), 7.17 (s, 1H), 7.23 (dd, 1H), 7.76 (d, 1H), 7.80 (d, 1H), 7.95 (s, 2H, NH$_2$).

Example 33

Sulfamic acid, 2-cyclodecyl-benzothiophene-6-yl ester mp 98° C.
$^1$H-NMR (DMSOd$_6$): 1.30-2.10 (m, 18H), 3.31 (m, 1H), 7.20 (s, 1H), 7.23 (dd, 1H), 7.76 (d, 1H), 7.79 (d, 1H), 7.96 (s, 2H, NH$_2$).

Example 34

Sulfamic acid, 2-(4-methylcyclohexyl)-benzothiophene-6-yl ester mp 132° C.
$^1$H-NMR (DMSOd$_6$): 0.75-2.15 (m, 12H), 2.55 (m, 1H), 7.25 (s, 1H), 7.55 (dd, 1H), 7.60 (d, 1H), 7.70 (d, 1H), 8.25 (s, 2H, NH$_2$).

Example 35

Sulfamic acid, 2-(2-methylcyclohexyl)-benzothiophene-6-yl ester mp 110° C.
$^1$H-NMR (DMSOd$_6$): 0.65-2.30 (m, 12H), 3.15 (m, 1H), 7.05-7.35 (m, 12H), 7.70-7.89 (m, 2H), 7.97 (s, 2H, NH$_2$).

Example 36

Sulfamic acid, 2-(2,2-dimethylcyclopentyl)-benzothiophene-6-yl ester mp 72° C.
$^1$H-NMR (DMSOd$_6$): 0.70 (s, 3H), 1.10 (s, 3H), 1.45-2.30 (m, 6H), 3.02 (dd, 11H), 7.20 (s, 1H), 7.23 (dd, 1H), 7.78 (d, 1H), 7.80 (s, 1H), 7.96 (s, 2H, NH$_2$).

Example 37

Sulfamic acid, 2-(2-adamantyl)-benzothiophene-6-yl ester mp 185° C.
$^1$H-NMR (DMSOd$_6$): 1.50-2.40 (m, 12H), 3.37 (br s, 1H), 7.24 (m, 2H), 7.80 (d, 1H), 7.82 (s, 1H), 7.97 (s, 2H, NH$_2$).

Example 38

Sulfamic acid, 2-propyl-benzothiophene-6-yl ester mp 112° C.
$^1$H-NMR (DMSOd$_6$): 0.96 (t, 3H), 1.70 (m, 2H), 2.88 (t, 2H), 7.19 (s, 1H), 7.24 (dd, 1H), 7.78 (d, 1H), 7.80 (s, 1H), 7.97 (s, 2H, NH$_2$).

Example 39

Sulfamic acid, 2-hexyl-benzothiophene-6-yl ester

Mp 125° C.
$^1$H-NMR (DMSOd$_6$): 0.95 (t, 3H), 1.10-1.80 (m, 8H), 2.88 (t, 2H), 7.19 (s, 1H), 7.22 (dd, 1H), 7.77 (d, 1H), 7.79 (s, 1H), 7.96 (s, 2H, NH$_2$).

Example 40

Sulfamic acid, 2-cyclohexylmethyl-benzothiophene-6-yl ester

Mp 115° C.
$^1$H-NMR (DMSOd$_6$): 0.80-1.80 (m, 8H), 2.78 (d, 2H), 7.16 (s, 1H), 7.24 (dd, 1H), 7.77 (d, 1H), 7.79 (s, 1H), 7.97 (s, 2H, NH$_2$).

Example 41

Sulfamic acid, 2-cycloheptylmethyl-benzothiophene-6-yl ester mp 90° C.
$^1$H-NMR (DMSOd$_6$): 1.00-2.00 (m, 13H), 2.82 (d, 2H), 7.18 (s, 1H), 7.22 (dd, 1H), 7.78 (d, 1H), 7.80 (s, 1H), 7.97 (s, 2H, NH$_2$).

PREPARATION OF MONO OR DI-OXIDIZED MONOSUBSTITUTED COMPOUNDS (8)

Example 42

Sulfamic acid, 2-cyclohexyl-benzothiophene-6-yl-1-oxide ester

To a solution of sulfamic acid, 2-cyclohexyl-benzothiophene-6-yl ester (1.00 g, 3.21 mmol) in dichloromethane (20 ml) and trifluoroacetic acid (5 ml) was added 35% aqueous hydrogen peroxide (0.35 ml, 3.42 mmol, 1.05 equivalent). After 2 h at 50° C. the mixture was hydrolysed with saturated aqueous NaHCO$_3$, extracted with dichloromethane, dried over Na$_2$SO$_4$, filtered, and concentrated under vacuum to give the crude product. Flash chromatography on silica gel (toluene/1,4-dioxan: 6/4) yielded a limpid oil which was crystallised from ethanol to give the title product (0.25 g, 24%, mp 110° C.).

$^1$H-NMR (DMSOd$_6$): 1.10-2.15 (m, 10H), 2.72 (m, 1H), 7.10 (s, 1H), 7.45 (dd, 1H), 7.64 (d, 1H), 7.84 (d, 1H), 8.16 (s, 2H, NH$_2$).

Using the same procedure but replacing the sulfamic acid, 2-cyclohexyl-benzothiophene-6-yl ester by:

Sulfamic acid, 2-cyclodecyl-benzothiophene-6-yl ester, the following compound was obtained:

Example 43

Sulfamic acid, 2-cyclodecyl-benzothiophene-6-yl-1-oxide ester mp 146° C.
$^1$H-NMR (DMSOd$_6$): 1.35-2.10 (m, 18H), 3.12 (m, 1H), 7.15 (s, 1H), 7.45 (dd, 1H), 7.62 (d, 1H), 7.83 (d, 1H), 8.15 (s, 2H, NH$_2$).

Using the procedure of example 42 but with 2.2 equivalents of hydrogen peroxide, the following compound was obtained:

Example 44

Sulfamic acid, 2-cyclohexyl-benzothiophene-6-yl-1,1-dioxide ester mp 180° C.
$^1$H-NMR (DMSOd$_6$): 1.15-2.15 (m, 10H), 2.52 (m, 1H), 7.30 (s, 1H), 7.53 (dd, 1H), 7.63 (d, 1H), 7.71 (d, 1H), 8.25 (s, 2H, NH$_2$).

Using the same procedure but replacing the sulfamic acid, 2-cyclohexyl-benzothiophene-6-yl ester by:
Sulfamic acid, 2-cycloheptyl-benzothiophene-6-yl ester
Sulfamic acid, 2-cyclooctyl-benzothiophene-6-yl ester
Sulfamic acid, 2-cyclodecyl-benzothiophene-6-yl ester
Sulfamic acid, 2-(4-methylcyclohexyl)-benzothiophene-6-yl ester
Sulfamic acid, 2-(2-methylcyclohexyl)-benzothiophene-6-yl ester
Sulfamic acid, 2-(2,2-dimethylcyclopentyl)-benzothiophene-6-yl ester
Sulfamic acid, 2-(2-adamantyl)-benzothiophene-6-yl ester
Sulfamic acid, 2-propyl-benzothiophene-6-yl ester
Sulfamic acid, 2-hexyl-benzothiophene-6-yl ester
Sulfamic acid, 2-cyclohexylmethyl-benzothiophene-6-yl ester
Sulfamic acid, 2-cycloheptylmethyl-benzothiophene-6-yl ester, the following compounds were respectively obtained:

Example 45

Sulfamic acid, 2-cycloheptyl-benzothiophene-6-yl-1,1-dioxide ester mp 137° C.
$^1$H-NMR (DMSOd$_6$): 1.35-2.15 (m, 12H), 2.75 (m, 1H), 7.32 (s, 1H), 7.52 (dd, 1H), 7.61 (d, 1H), 7.70 (d, 1H), 8.25 (s, 2H, NH$_2$).

Example 46

Sulfamic acid, 2-cyclooctyl-benzothiophene-6-yl-1,1-dioxide ester mp 122° C.
$^1$H-NMR (DMSOd$_6$): 1.35-2.10 (m, 14H), 2.81 (m, 1H), 7.32 (s, 1H), 7.52 (dd, 1H), 7.61 (d, 1H), 7.70 (d, 1H), 8.22 (s, 2H, NH$_2$).

Example 47

Sulfamic acid, 2-cyclodecyl-benzothiophene-6-yl-1,1-dioxide ester mp 102° C.
$^1$H-NMR (DMSOd$_6$): 1.35-2.10 (m, 18H), 2.97 (m, 1H), 7.38 (s, 1H), 7.52 (dd, 1H), 7.60 (d, 1H), 7.70 (d, 1H), 8.22 (s, 2H, NH$_2$).

Example 48

Sulfamic acid, 2-(4-methylcyclohexyl)-benzothiophene-6-yl-1,1-dioxide ester mp 170° C.
$^1$H-NMR (DMSOd$_6$): 0.75-2.20 (m, 12H), 2.83 (m, 1H), 7.18 (s, 1H), 7.22 (dd, 1H), 7.78 (d, 1H), 7.80 (d, 1H), 7.95 (s, 2H, NH$_2$).

Example 49

Sulfamic acid, 2-(2-methylcyclohexyl)-benzothiophene-6-yl-1,1-dioxide ester mp 92° C.
$^1$H-NMR (DMSOd$_6$): 0.70-2.45 (m, 12H), 2.85 (m, 1H), 7.25 (s, 1H), 7.52 (m, 3H), 8.25 (s, 2H, NH$_2$).

Example 50

Sulfamic acid, 2-(2,2-dimethylcyclopentyl)-benzothiophene-6-yl-1,1-dioxide ester mp 172° C.
$^1$H-NMR (DMSOd$_6$): 0.90 (s, 3H), 1.16 (s, 3H), 1.50-2.15 (m, 6H), 2.66 (t, 1H), 7.49 (s, 1H), 7.52 (dd, 1H), 7.61 (d, 11H), 7.70 (d, 1H), 8.24 (s, 2H, NH$_2$).

Example 51

Sulfamic acid, 2-(2-adamantyl)-benzothiophene-6-yl-1,1-dioxide ester mp 230° C.
$^1$H-NMR (DMSOd$_6$): 1.45-2.45 (m, 14H), 3.04 (br s, 1H), 7.38 (s, 1H), 7.53 (d, 1H), 7.64 (d, 1H), 7.70 (d, 1H), 8.25 (s, 2H, NH$_2$).

Example 52

Sulfamic acid, 2-propyl-benzothiophene-6-yl-1,1-dioxide ester mp 159° C.
$^1$H-NMR (DMSOd$_6$): 0.99 (t, 3H), 1.70 (m, 2H), 2.49 (t, 2H), 7.29 (s, 1H), 7.52 (dd, 1H), 7.63 (d, 1H), 7.73 (d, 1H), 8.50 (s, 2H, NH$_2$).

Example 53

Sulfamic acid, 2-hexyl-benzothiophene-6-yl-1,1-dioxide ester mp 98° C.
$^1$H-NMR (DMSOd$_6$): 0.85 (t, 3H), 1.10-1.80 (m, 8H), 2.50 (t, 2H), 7.30 (s, 1H), 7.52 (dd, 1H), 7.62 (d, 1H), 7.73 (d, 1H), 8.27 (s, 2H, NH$_2$).

Example 54

Sulfamic acid, 2-cyclohexylmethyl-benzothiophene-6-yl-1,1-dioxide ester mp 132° C.
$^1$H-NMR (DMSOd$_6$): 0.80-1.95 (m, 11H), 2.40 (d, 2H), 7.30 (s, 1H), 7.53 (dd, 1H), 7.62 (d, 1H), 7.72 (d, 11H), 8.25 (s, 2H, NH$_2$).

Example 55

Sulfamic acid, 2-cycloheptylmethyl-benzothiophene-6-yl-1,1-dioxide ester mp 135° C.
$^1$H-NMR (DMSOd$_6$): 1.00-2.15 (m, 13H), 2.45 (d, 2H), 7.29 (s, 1H), 7.53 (dd, 1H), 7.62 (d, 1H), 7.73 (d, 1H), 8.25 (s, 2H, NH$_2$).

PREPARATION OF DISUBSTITUTED 6-METHOXY-BENZOTHIOPHENE (9)

Example 56

2-cycloheptyl-6-methoxy-2,7-methyl-benzothiophene

To a solution of 2-cycloheptyl-6-methoxy-benzothiophene (2.00 g, 7.69 mmol) in dry THF (20 ml) at −70° C. was added dropwise a 2.5 M solution of n-butyl lithium in hexane (5 ml, 12.16 mmol). Then, the mixture was warmed to −30° C. during 10 min and chilled at −70° C. for the addition of iodomethane (1.0 ml, 15.38 mmol). The mixture was warmed to room temperature overnight. It was hydrolysed with saturated aqueous NH$_4$Cl, extracted with ethyl acetate, dried (Na$_2$SO$_4$), filtered and concentrated under vacuum to give 2.1 g of an oil. Flash chromatography on silica gel (heptane/ethyl acetate: 1/1) yielded a limpid oil (1.50 g, 72%) which was used without further purification.

$^1$H-NMR (DMSOd$_6$): 1.35-2.15 (m, 12H), 2.29 (s, 3H), 3.00 (m, 1H), 3.80 (s, 3H), 7.00 (s, 1H), 7.04 (d, 1H), 7.49 (d, 1H).

Using the same procedure but replacing iodomethane by: bromobutane, the following compound was obtained:

Example 57

2-cycloheptyl-6-methoxy-7-butyl-benzothiophene $^1$H-NMR (DMSOd$_6$): 0.90 (t, 3H), 1.10-2.20 (m, 16H), 2.75 (t, 2H), 3.04 (m, 11H), 3.80 (s, 3H), 7.00 (s, 1H), 7.05 (d, 1H), 7.51 (d, 1H).

Example 58

7-methoxy-1,2,3,4-tetrahydro-dibenzothiophene

This compound was prepared using the conditions described by Oliveira. M (*Tetrahedron*, 2002, 58, 1709-18).
$^1$H-NMR (CDCl$_3$): 1.92 (m, 4H), 2.72 (m, 2H), 2.83 (m, 2H), 3.89 (s, 3H), 6.97 (dd, 1H), 7.30 (d, 1H), 7.47 (d, 1H).

PREPARATION OF DISUBSTITUTED BENZOTHIOPHENE-OL (10)

Following the procedure used for the monosubstituted compounds, but replacing 2-cyclohexyl-6-methoxy-benzothiophene by:
2-cycloheptyl-2-methyl-6-methoxy-benzothiophene
2-cycloheptyl-6-methoxy-3-butyl-benzothiophene
7-methoxy-1,2,3,4-tetrahydro-dibenzothiophene,
the following compounds were respectively obtained:

Example 59

2-cycloheptyl-7-methyl-benzothiophene-6-ol mp 96° C.
$^1$H-NMR (DMSOd$_6$): 1.30-2.15 (m, 12H), 2.44 (s, 3H), 3.01 (m, 1H), 6.87 (d, 1H), 6.97 (s, 1H), 7.34 (d, 1H), 9.31 (s, 1H, OH).

Example 60

2-cycloheptyl-7-butyl-benzothiophene-6-ol limpid oil $^1$H-NMR (DMSOd$_6$): 0.92 (t, 3H), 1.15-2.20 (m, 16H), 2.80 (t, 2H), 3.02 (m, 1H), 6.85 (d, 1H), 6.95 (s, 1H), 7.32 (d, 1H), 9.22 (s, 1H, OH).

Example 61

1,2,3,4-tetrahydro-dibenzothiophene-7-ol mp 116° C.
$^1$H-NMR (CDCl$_3$): 1.90 (m, 4H), 2.68 (m, 2H), 2.79 (m, 2H), 4.98 (br s, 1H, OH), 6.88 (dd, 1H), 7.20 (d, 1H), 7.42 (d, 1H).

PREPARATION OF SULFAMIC ACID DISUBSTITUTED BENZOTHIOPHENYL ESTER (11)

Following the procedure used for the monosubstituted compounds but replacing 2-cyclohexyl-benzothiophene-6-ol by:
2-cycloheptyl-2-methyl-benzothiophene-6-ol
2-cycloheptyl-2-butyl-benzothiophene-6-ol
1,2,3,4-tetrahydro-dibenzothiophene-7-ol,
the following compounds were respectively obtained:

Example 62

Sulfamic acid, 2-cycloheptyl-7-methyl-benzothiophene-6-yl ester mp 107° C.
$^1$H-NMR (DMSOd$_6$): 1.40-2.20 (m, 12H), 2.46 (s, 3H), 3.14 (m, 1H), 7.20 (s, 1H), 7.30 (dd, 1H), 7.60 (d, 1H), 8.00 (s, 2H, NH$_2$).

Example 63

Sulfamic acid, 2-cycloheptyl-7-butyl-benzothiophene-6-yl ester limpid oil $^1$H-NMR (DMSOd$_6$): 0.91 (t, 3H), 1.15-2.20 (m, 16H), 2.77 (t, 2H), 3.11 (m, 1H), 7.15 (s, 10H), 7.32 (d, 1H), 7.59 (d, 1H), 8.04 (s, 2H, NH$_2$).

Example 64

Sulfamic acid, 1,2,3,4-tetrahydro-dibenzothiophene-7-yl ester mp 165° C.
$^1$H-NMR (DMSOd$_6$): 1.87 (m, 4H), 2.70 (m, 2H), 2.82 (m, 2H), 7.28 (dd, 1H), 7.66 (d, 1H), 7.72 (d, 1H).

PREPARATION OF DIOXIDIZED DISUBSTITUTED COMPOUNDS (12)

Following the procedure used for the monosubstituted compounds but replacing the sulfamic acid, 2-cycloheptyl-benzothiophene-6-ol ester by:
  Sulfamic acid, 2-cycloheptyl-3-methyl-benzothiophene-6-ol ester
  Sulfamic acid, 2-cycloheptyl-3-butyl-benzothiophene-6-ol ester
  Sulfamic acid, 1,2,3,4-tetrahydro-dibenzothiophene-7-ol ester, the following compounds were respectively obtained:

Example 65

Sulfamic acid, 2-cycloheptyl-7-methyl-benzothiophene-6-yl-1,1-dioxide ester mp 90° C.
$^1$H-NMR (DMSOd$_6$): 1.30-2.20 (m, 12H), 2.48 (s, 3H), 2.76 (m, 1H), 7.28 (s, 1H), 7.41 (d, 1H), 7.52 (d, 1H), 8.27 (s, 2H, NH$_2$).

Example 66

Sulfamic acid, 2-cycloheptyl-7-butyl-benzothiophene-6-yl-1,1-dioxide ester limpid oil $^1$H-NMR (DMSOd$_6$): 0.91 (t, 3H), 1.15-2.15 (m, 16H), 2.75 (m, 1H), 2.90 (t, 2H), 7.25 (s, 1H), 7.40 (d, 1H), 7.56 (d, 1H), 8.31 (s, 2H, NH$_2$).

Example 67

Sulfamic acid, 1,2,3,4-tetrahydro-dibenzothiophene-7-yl-1,1-dioxide ester mp 229° C.
$^1$H-NMR (DMSO$_6$): 1.78 (m, 4H), 2.30-2.70 (m, 4H), 7.54 (dd, 1H), 7.61 (d, 1H), 7.74 (d, 11H).

Biological Test Results

Inhibition of Steroid Sulfatase In Vitro

Estrone sulfate (E$_1$S) is a major circulating plasma estrogen that is converted by the steroid sulfatase enzyme into estrone (E$_1$), which in turn can be transformed into estradiol (E$_2$) by enzymatic reduction. Steroid sulfatase activity is present in most tissues (uterus, liver, breast, etc.) and is significantly higher in malignant than in normal breast tissue. The close association of estrogens with the promotion of the growth and development of breast cancer has long been recognized, therefore steroid sulfatase appears as a potential target to inhibit in situ formation of estrogens.

Potent inhibitors of this enzyme, containing a sulfamate moiety which is believed to be involved in the irreversible inhibition of steroid sulfatase, have been synthesized. To date the most active compound is EMATE, estrone-3-sulfamate, but its estrogenic activity has rendered this compound unsuitable for use in the treatment of hormone-dependent-tumors. Numerous structurally diversified inhibitors of steroid sulfatase have been reported among which, 6,6,7-COUMATE emerged as a standard non-steroidal inhibitor lacking estrogenic properties.

In Vitro Results

Two in vitro models on whole cells were used. The JEG-3 cell line, derived from a human placental choriocarcinoma, is spontaneously very rich in human estrone sulfatase and therefore, a useful practical biological system to screen in a 96-well microplate format a large number of compounds and evaluate putative steroid sulfatase inhibitors in vitro. Despite a lower content in steroid sulfatase activity, the MCF-7 cells constitute another suitable model to test steroid sulfatase inhibitors on human breast adenocarcinoma cells. Moreover, these cells were used in the in vivo model of hormono-dependent induced xenografts.

Estrone Sulfatase Assay on Cells

Whole-cell assays were performed as originally described by Duncan et al. (Cancer Res., 1993, 53: 298-303) on intact MCF-7 cell monolayers. Assays were carried out with cells in logarithmic growth phase, on 96-well (JEG-3) or 24-well (MCF-7) microplates. Twenty-four hours (JEG-3) or 72 h (MCF-7) before studies, cells were seeded in decomplemented fetal calf serum (dFCS) supplemented medium. Then, the seeding medium was removed and the cells were rinsed with PBS to eliminate any trace of dFCS. Then, $^3$H-E$_1$S was added, followed by test compounds ranging from $10^{-12}$ M to $10^{-5}$ M. After 4 h (JEG-3) or 20 h (MCF-7) of treatment, the medium was transferred into either 96-deep-well microplates (JEG-3) or plastic tubes (MCF-7) and centrifuged at 200×g for 10 min to pellet cells before toluene extraction. A fraction of medium was used for toluene extraction in order to separate conjugated substrate and non-conjugated products. The radioactivity in the toluene phase was measured by liquid scintillation counting (LSC). Finally, estrone sulfatase activity was expressed in pmoles of $^3$H-E$_1$ + $^3$H-E$_2$ formed per 4 or 20 hours and per µg DNA and estrone sulfatase inhibition in percentage of control activity without inhibitor. A non linear fit analysis (GraphPad Prism Software) of % inhibition vs. inhibitor concentrations allowed for the determination of 50% inhibitory concentration (IC$_{50}$): the lowest IC$_{50}$ corresponds to the most potent inhibitors (Table 1).

TABLE 1

Inhibition of estrone sulfatase on whole-cell assays

| | JEG-3 cells | | MCF-7 cells | |
|---|---|---|---|---|
| Compounds | IC$_{50}$ (nM) ± S.E.M. | n | IC$_{50}$ (nM) ± S.E.M. | n |
| EMATE | 3.2 ± 0.2 | 4 | 0.06 ± 0.01 | 18 |
| 6,6,7-COUMATE | 4.5 ± 0.6 | 37 | 0.33 ± 0.06 | 24 |
| Ex 30 | 78.8 ± 39.8 | 5 | | |
| Ex 31 | 101.8 ± 58.0 | 5 | | |
| Ex 32 | 433.7 ± 94.8 | 5 | | |
| Ex 33 | 743.8 ± 139.6 | 5 | | |
| Ex 34 | 317.7 ± 42.9 | 5 | | |
| Ex 35 | 146.8 ± 16.3 | 4 | | |
| Ex 36 | 128.5 ± 14.2 | 4 | | |
| Ex 37 | 92.4 ± 15.6 | 5 | | |
| Ex 42 | 7.0 ± 1.2 | 5 | 0.16 ± 0.03 | 4 |
| Ex 44 | 10.9 ± 2.6 | 5 | 0.24 ± 0.05 | 4 |
| Ex 47 | 52.1 ± 4.4 | 5 | 0.08 ± 0.01 | 4 |
| Ex 48 | 7.6 ± 1.3 | 5 | 0.09 ± 0.02 | 4 |
| Ex 49 | 2.6 ± 0.4 | 4 | | |
| Ex 50 | 2.5 ± 0.5 | 4 | | |
| Ex 52 | 24.7 ± 5.0 | 5 | | |
| Ex 53 | 12.5 ± 3.3 | 5 | | |
| Ex 54 | 10.0 ± 1.2 | 4 | 0.10 ± 0.03 | 4 |
| Ex 55 | 7.7 ± 0.4 | 4 | 0.05 ± 0.01 | 6 |
| Ex 64 | 565.8 ± 129.6 | 5 | | |
| Ex 65 | 31.7 ± 9.9 | 4 | | |

Among the tested compounds, Ex 42, Ex 44, Ex 48, Ex 49, Ex 50, Ex 54 and Ex 55 showed a strong inhibition (IC$_{50}$ of about 10 nM) of human estrone sulfatase activity in JEG-3 cells. These compounds were checked for residual estrogenic activity in vivo in the classical uterotrophic assay after 3-day administration by oral route in prepubescent female rats.

Inhibition of Steroid Sulfatase In Vivo

Residual Estrogenic Activity In Vivo

Prepubescent female rats were orally treated at 1 mg/rat/day for 3 days. On the day following the last treatment, uteri were removed and wet weight were recorded.

The results are expressed as % of stimulation of uterus weight in comparison with controls.

TABLE 2 residual estrogenic activity

| Compound | % stimulation | Number of animals |
|---|---|---|
| 6,6,7 COUMATE | 3% | 16 |
| Ex 42 | 0% | 8 |
| Ex 44 | 0% | 8 |
| Ex 47 | 4% | 8 |
| Ex 48 | 3% | 8 |
| Ex 49 | 8% | 8 |
| Ex 50 | 24% | 8 |
| Ex 54 | 6% | 8 |
| Ex 55 | 3% | 8 |

Antiuterotrophic/Antisulfatase Activity

A short model, derived from Purohit's method, was developed for the evaluation in vivo of nonestrogenic steroid sulfatase inhibitors.

Wistar female rats were ovariectomized and left to rest for 4 weeks. Prior to treatment, the absence of cyclicity was checked by vaginal smears.

Animals were supplemented with estrone sulfate ($E_1S$) at 50 µg/kg/day s.c., alone or combined with oral administration of potential sulfatase inhibitors, at 1 mg/kg/day for 4 days. The uteri were removed, freed of adjacent tissue and wet weighed.

The results are expressed as % of inhibition of the $E_1S$ induced stimulation.

TABLE 3 antiuterotrophic activity

| Compound | % inhibition | Number of animals |
|---|---|---|
| 6,6,7 COUMATE | 86% | 48 |
| Ex 42 | 38% | 8 |
| Ex 44 | 70% | 8 |
| Ex 47 | 62% | 8 |
| Ex 48 | 60% | 8 |
| Ex 54 | 49% | 8 |
| Ex 55 | 81% | 16 |

Ex 55 was chosen as potential inhibitor of steroid sulfatase activity because of lack of estrogenicity and significant inhibition of $E_1S$ stimulated uterus weight. These in vivo results were in good accordance with in vitro results obtained in JEG-3 and MCF-7 whole-cell assays.

Evaluation of the Potency of Ex 55

The activity of Ex 55 on $E_1S$ stimulated uterus weight was evaluated in relation to the standard inhibitor 6,6,7 COUMATE from 0.03 mg/kg/day to 1 mg/kg/day p.o.

In this study, a last administration was performed 24 hours before the necropsy for $E_1S$ and $E_2$ serum levels assays. The uteri were removed, freed of adjacent tissue, wet weighed and immediately deep frozen until the determination of sulfatase activity.

Inhibition of $E_1S$ Stimulated Uterus Weight

TABLE 4

| Dose mg/kg/day | 6,6,7 COUMATE | Ex 55 |
|---|---|---|
| 0.03 | 0% | 0% |
| 0.1 | 13% | 0% |
| 0.3 | 52% | 36% |
| 1 | 84% | 72% |

Measure of Estrone Sulfatase Activity in the Uterus

Estrone sulfatase activity was measured according to the method described by Purohit et al., with slight modifications. Briefly, uteri were thawed, weighed and homogenized. Aliquots of the supernatant were treated with dextran-coated charcoal and assayed for sulfatase. $E_1S$ activity was assessed after 30 min of incubation with 5 nM of $^3H-E_1S$ and 20 µM of unlabelled $E_1S$ as substrate. Radioactivity was measured by LSC.

Estrone sulfatase activity was expressed as pmol/h/mg protein and reported as percentage of inhibition versus $E_1S$.

TABLE 5

| Dose mg/kg/day | 6,6,7 COUMATE | Ex 55 |
|---|---|---|
| 0.03 | 36% | 19% |
| 0.1 | 78% | 64% |
| 0.3 | 96% | 96% |
| 1 | 97% | 97% |

Serum Estrogen Levels $E_1S$ and $E_2$ levels were determined according to the supplier's standard method (DSL, Webster, Tex., USA).

TABLE 6

| | $E_1S$ levels (ng/ml) | |
|---|---|---|
| Dose mg/kg/day | 6,6,7 COUMATE | Ex 55 |
| 0 | 6.3 ± 0.3 | |
| 0.03 | 24 ± 3.1 | 17 ± 2.5 |
| 0.1 | 26 ± 2.6 | 21 ± 2.4 |
| 0.3 | 59 ± 6.4 | 69 ± 5.9 |
| 1 | 80 ± 5.7 | 83 ± 2.5 |

TABLE 7

| | $E_2$ levels (pg/ml) | |
|---|---|---|
| Dose mg/kg/day | 6,6,7 COUMATE | Ex 55 |
| 0 | 7.8 ± 0.7 | |
| 0.03 | 33 ± 5.8 | 31 ± 2.8 |
| 0.1 | 28 ± 2.5 | 28 ± 1.3 |
| 0.3 | 18 ± 1.1 | 22 ± 1.2 |
| 1 | 16 ± 1.5 | 15 ± 0.9 |

Hormono-Dependent Induced Xenografts

MCF-7 cells, derived from human breast adenocarcinoma, were injected subcutaneously in ovariectomized athymic nude mice supplemented with estrone sulfate (pellets 0.5 mg/90 day release). Xenograft volumes were determined once weekly. When tumor volumes reached a significant increase, 6,6,7 COUMATE and Ex 55 were orally administered at 0.1 mg/kg/day for 6 weeks.

Xenografts were measured, removed, weighed, and deep frozen until the determination of steroid sulfatase activity.

TABLE 8

Xenograft volume (mm³)

| Treatment | Xenograft volume after 6 week treatment |
|---|---|
| Control placebo | 71 ± 8.2 |
| E₁S pellet (0.5 mg/90 day release) | 1816 ± 337 |
| E₁S + 6,6,7 COUMATE 0.1 mg/kg/day | 1854 ± 243 |
| E₁S + Ex 55 0.1 mg/kg/day | 1488 ± 233 |

6,6,7 COUMATE did not inhibit the E₁S induced stimulation after 6 weeks oral administration at 0.1 mg/kg/day. By contrast 18% inhibition were obtained with Ex 55 at the same dose level.

TABLE 9

Xenograft weight (mg)

| Treatment | Xenograft weight after 6 week treatment |
|---|---|
| Control placebo | 31 ± 3.8 |
| E₁S pellet (0.5 mg/90 day release) | 1350 ± 277 |
| E₁S + 6,6,7 COUMATE 0.1 mg/kg/day | 1467 ± 191 |
| E₁S + Ex 55 0.1 mg/kg/day | 877 ± 185 |

6,6,7 COUMATE did not inhibit xenograft weight while 35% inhibition were obtained with Ex 55.

TABLE 10

Xenograft steroid sulfatase activity (pmol/h/mg protein)

| Treatment | Sulfatase activity |
|---|---|
| E₁S pellet (0.5 mg/90 day release) | 1653 ± 101 |
| E₁S + 6,6,7 COUMATE 0.1 mg/kg/day | 540 ± 54 |
| E₁S + Ex 55 0.1 mg/kg/day | 263 ± 17 |

The inhibition of intratumoral steroid sulfatase activity was higher with Ex 55 (84%) than with 6,6,7 COUMATE (67%).

The invention claimed is:

1. A compound of formula (Ia) or formula (Ib):

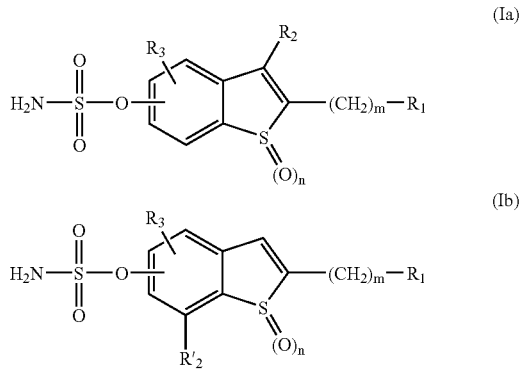

wherein:
R₁ is hydrogen, a (C₁-C₆)alkyl, a (C₂-C₆)alkene, a (C₃-C₁₂)cycloalkyl or a (C₃-C₁₂)cycloalkene wherein the cycloalkyl and the cycloalkene are optionally mono- or disubstituted with a (C₁-C₄) alkyl;

R₂ is hydrogen,
R'₂ is a (C₁-C₆)alkyl or a (C₃-C₁₂)cycloalkyl;
R₃ is hydrogen, a (C₁-C₆)alkoxy or a halogen;
m is 0, 1, 2;
n is 0, 1, 2;
when m is 0, R₁ and R₂ can also form together a group —(CH₂)ₚ— in which p is 3, 4 or 5;
the dotted line indicates that the sulfamate group is in position 5- or 6- of the benzothiophene ring.

2. The compound according to claim 1, wherein R₁ is hydrogen, a (C₁-C₆)alkyl, or a (C₃-C₁₂)cycloalkyl which is optionally mono- or disubstituted with a (C₁-C₄) alkyl.

3. The compound according to claim 2, wherein R₁ is a (C₃-C₁₁)cycloalkyl which is optionally mono- or disubstituted with a (C₁-C₄)alkyl.

4. The compound according to claim 1, wherein m is 0 or 1.

5. The compound according to claim 1, wherein R₃ is hydrogen.

6. The compound according claim 1, wherein n is 0 or 2.

7. The compound according to claim 1, wherein the sulfamate group is in position 6- of the benzothiophene ring.

8. Sulfamate benzothiophene derivative produced by a process comprising the steps of:
1) converting 6-methoxy-benzothiophene (3):

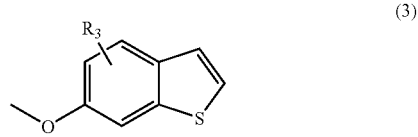

in which R₃ is hydrogen, a (C₁-C₆) alkoxy or a halogen or the corresponding 5-methoxy-benzothiophene to the corresponding monobromo derivative with N-bromosuccinimide and APTS using standard conditions;

2) transforming said monobromo derivative into an organomagnesium bromide and then condensing it with a ketone or an aldehyde selected from the group consisting of cyclopentanone, cyclohexanone, cycloheptanone, cyclooctanone, cyclodecanone, 4-methylcyclohexanone, 2-methylcyclohexanone, 2,2-dimethyl-cyclopentanone, 2-adamantanone, propanal, hexanal, cyclohexane-carboxaldehyde, cycloheptanecarboxaldehyde to afford the corresponding substituted methoxybenzothiophene using standard conditions;

3) optionally alkylating the corresponding substituted methoxybenzothiophene using conventional conditions to afford the corresponding substituted methoxybenzothiophene bearing a (C₁-C₆)alkyl or a (C₃-C₁₂)cycloalkyl;

4) deprotecting the substituted methoxybenzothiophene obtained in step 2) or in step 3) with tribromoborane under conventional conditions;

5) transforming the resulting hydroxy compound into the corresponding sulfamate by treatment with sodium hydride, with amidochlorosulfonic acid or by reaction with sulfamoyl chloride in dimethylacetamide; and 6) optionally oxidating the resulting compound by hydrogen peroxide in trifluoroacetic acid using conventional conditions.

9. Sulfamate benzothiophene derivative according to claim 8 with a melting point of 128° C., said derivative being obtainable by the steps of:
1) converting the 6-methoxy-benzothiophene (3) to the corresponding monobromo derivative with N-bromosuccinimide and p-toluenesulfonic acid;
2) transforming said monobromo derivative into an organomagnesium bromide with Mg under argon in Et₂O and then condensing it with cyclohexanone in Et$_2$O to afford the corresponding hydroxy substituted methoxybenzothiophene using standard conditions;
3) treating said hydroxy substituted methoxybenzothiophene with triethylsilane under argon in dichloromethane to afford the corresponding substituted methoxybenzothiophene;
4) adding the substituted methoxybenzothiophene obtained in step 3) in solution in dichloromethane to a solution of boron tribromide to afford the corresponding hydroxy benzothiophene; 5) transforming said hydroxy compound into the corresponding sulfamate by treatment with sodium hydride and amidochlorosulfonic acid.

10. Sulfamate benzothiophene derivative according to claim 8, with a melting point of 110° C., said derivative being obtainable by the steps of:
1) converting the 6-methoxy-benzothiophene (3) to the corresponding monobromo derivative with N-bromosuccinimide and p-toluenesulfonic acid;
2) transforming said monobromo derivative into an organomagnesium bromide with Mg under argon in Et$_2$O and then condensing it with cyclohexanone in Et$_2$O to afford the corresponding hydroxy substituted methoxybenzothiophene using standard conditions;
3) treating said hydroxy substituted methoxybenzothiophene with triethylsilane under argon in dichloromethane to afford the corresponding substituted methoxybenzothiophene;
4) adding the substituted methoxybenzothiophene obtained in step 3) in solution in dichloromethane to a solution of boron tribromide to afford the corresponding hydroxy benzothiophene;
5) transforming said hydroxy compound into the corresponding sulfamate by treatment with sodium hydride and amidochlorosulfonic acid;
6) oxidizing the resulting compound by 1.05 equivalents of hydrogen peroxide in trifluoroacetic acid and dichloromethane.

11. Sulfamate benzothiophene derivative according to claim 8, with a melting point of 98° C., said derivative being obtainable by:
1) converting the 6-methoxy-benzothiophene (3) to the corresponding monobromo derivative with N-bromosuccinimide and p-toluenesulfonic acid;
2) transforming said monobromo derivative into an organomagnesium bromide with Mg under argon in Et$_2$O and then condensing it with cyclodecanone in Et$_2$O to afford the corresponding hydroxy substituted methoxybenzothiophene using standard conditions;
3) treating said hydroxy substituted methoxybenzothiophene with triethylsilane under argon in dichloromethane to afford the corresponding substituted methoxybenzothiophene;
4) adding the substituted methoxybenzothiophene obtained in step 3) in solution in dichloromethane to a solution of boron tribromide to afford the corresponding hydroxy benzothiophene;
5) transforming said hydroxy compound into the corresponding sulfamate by treatment with sodium hydride and amidochlorosulfonic acid.

12. Sulfamate benzothiophene derivative according to claim 8, with a melting point of 146° C., said derivative being obtainable by:
1) converting the 6-methoxy-benzothiophene (3) to the corresponding monobromo derivative with N-bromosuccinimide and p-toluenesulfonic acid;
2) transforming said monobromo derivative into an organomagnesium bromide with Mg under argon in Et$_2$O and then condensing it with cyclodecanone in Et$_2$O to afford the corresponding hydroxy substituted methoxybenzothiophene using standard conditions;
3) treating said hydroxy substituted methoxybenzothiophene with triethylsilane under argon in dichloromethane to afford the corresponding substituted methoxybenzothiophene;
4) adding the substituted methoxybenzothiophene obtained in step 3) in solution in dichloromethane to a solution of boron tribromide to afford the corresponding hydroxy benzothiophene;
5) transforming said hydroxy compound into the corresponding sulfamate by treatment with sodium hydride and amidochlorosulfonic acid;
6) oxidizing the resulting compound by 1.05 equivalents of hydrogen peroxide in trifluoroacetic acid and dichloromethane.

13. Sulfamate benzothiophene derivative according to claim 8, with a melting point of 180° C., said derivative being obtainable by the steps of:
1) converting the 6-methoxy-benzothiophene (3) to the corresponding monobromo derivative with N-bromosuccinimide and p-toluenesulfonic acid;
2) transforming said monobromo derivative into an organomagnesium bromide with Mg under argon in Et$_2$O and then condensing it with cyclohexanone in Et$_2$O to afford the corresponding hydroxy substituted methoxybenzothiophene using standard conditions;
3) treating said hydroxy substituted methoxybenzothiophene with triethylsilane under argon in dichloromethane to afford the corresponding substituted benzothiophene;
4) adding the substituted methoxybenzothiophene obtained in step 3) in solution in dichloromethane to a solution of boron tribromide to afford the corresponding hydroxy benzothiophene;
5) transforming said hydroxy compound into the corresponding sulfamate by treatment with sodium hydride and amidochlorosulfonic acid;
6) oxidizing the resulting compound by 2.2 equivalents of hydrogen peroxide in trifluoroacetic acid and dichloromethane.

14. Sulfamate benzothiophene derivative according to claim 8, with a melting point of 132° C., said derivative being obtainable by the steps of:
1) converting the 6-methoxy-benzothiophene (3) to the corresponding monobromo derivative with N-bromosuccinimide and p-toluenesulfonic acid;
2) transforming said monobromo derivative into an organomagnesium bromide with Mg under argon in Et$_2$O and then condensing it with cycloheptanone in Et$_2$O to afford the corresponding hydroxy substituted methoxybenzothiophene using standard conditions;
3) treating said hydroxy substituted methoxybenzothiophene with triethylsilane under argon in dichloromethane to afford the corresponding substituted methoxybenzothiophene;
4) adding the substituted methoxybenzothiophene obtained in step 3) in solution in dichloromethane to a solution of boron tribromide to afford the corresponding hydroxy benzothiophene;
5) transforming said hydroxy compound into the corresponding sulfamate by treatment with sodium hydride and amidochlorosulfonic acid.

15. Sulfamate benzothiophene derivative according to claim 8, with a melting point of 137° C., said derivative being obtainable by the steps of:
1) converting the 6-methoxy-benzothiophene (3) to the corresponding monobromo derivative with N-bromosuccinimide and p-toluenesulfonic acid;

2) transforming said monobromo derivative into an organomagnesium bromide with Mg under argon in Et$_2$O and then condensing it with cycloheptanone in Et$_2$O to afford the corresponding hydroxy substituted methoxybenzothiophene using standard conditions;
3) treating said hydroxy substituted methoxybenzothiophene with triethylsilane under argon in dichloromethane to afford the corresponding substituted methoxybenzothiophene;
4) adding the substituted methoxybenzothiophene obtained in step 3) in solution in dichloromethane to a solution of boron tribromide to afford the corresponding hydroxy benzothiophene;
5) transforming said hydroxy compound into the corresponding sulfamate by treatment with sodium hydride and amidochlorosulfonic acid;
6) oxidizing the resulting compound by 2.2 equivalents of hydrogen peroxide in trifluoroacetic acid and dichloromethane.

16. Sulfamate benzothiophene derivative according to claim 8 with a melting point of 126° C., said derivative obtainable by the steps of:
   1) converting the 6-methoxy-benzothiophene (3) to the corresponding monobromo derivative with N-bromosuccinimide and p-toluenesulfonic acid;
   2) transforming said monobromo derivative into an organomagnesium bromide with Mg under argon in Et$_2$O and then condensing it with cyclooctanone in Et$_2$O to afford the corresponding hydroxy substituted methoxybenzothiophene using standard conditions;
   3) treating said hydroxy substituted methoxybenzothiophene with triethylsilane under argon in dichloromethane to afford the corresponding substituted methoxybenzothiophene;
   4) adding the substituted methoxybenzothiophene obtained in step 3) in solution in dichloromethane to a solution of boron tribromide to afford the corresponding hydroxy benzothiophene;
   5) transforming said hydroxy compound into the corresponding sulfamate by treatment with sodium hydride and amidochlorosulfonic acid.

17. Sulfamate benzothiophene derivative according to claim 8 with a melting point of 122° C., said derivative being obtainable by the steps of:
   1) converting the 6-methoxy-benzothiophene (3) to the corresponding monobromo derivative with N-bromosuccinimide and p-toluenesulfonic acid;
   2) transforming said monobromo derivative into an organomagnesium bromide with Mg under argon in Et$_2$O and then condensing it with cyclooctanone in Et$_2$O to afford the corresponding hydroxy substituted methoxybenzothiophene using standard conditions;
   3) treating said hydroxy substituted methoxybenzothiophene with triethylsilane under argon in dichloromethane to afford the corresponding substituted methoxybenzothiophene;
   4) adding the substituted methoxybenzothiophene obtained in step 3) in solution in dichloromethane to a solution of boron tribromide to afford the corresponding hydroxy benzothiophene;
   5) transforming said hydroxy compound into the corresponding sulfamate by treatment with sodium hydride and amidochlorosulfonic acid;
   6) oxidizing the resulting compound by 2.2 equivalents of hydrogen peroxide in trifluoroacetic acid and dichloromethane.

18. Sulfamate benzothiophene derivative according to claim 8 with a melting point of 102° C., said derivative being obtainable by the steps of:
   1) converting the 6-methoxy-benzothiophene (3) to the corresponding monobromo derivative with N-bromosuccinimide and p-toluenesulfonic acid;
   2) transforming said monobromo derivative into an organomagnesium bromide with Mg under argon in Et$_2$O and then condensing it with cyclodecanone in Et$_2$O to afford the corresponding hydroxy substituted methoxybenzothiophene using standard conditions;
   3) treating said hydroxy substituted methoxybenzothiophene with triethylsilane under argon in dichloromethane to afford the corresponding substituted methoxybenzothiophene;
   4) adding the substituted methoxybenzothiophene obtained in step 3) in solution in dichloromethane to a solution of boron tribromide to afford the corresponding hydroxy benzothiophene;
   5) transforming said hydroxy compound into the corresponding sulfamate by treatment with sodium hydride and amidochlorosulfonic acid;
   6) oxidizing the resulting compound by 2.2 equivalents of hydrogen peroxide in trifluoroacetic acid and dichloromethane.

19. Sulfamate benzothiophene derivative according to claim 8 with a melting point of 132° C., said derivative being obtainable by the steps of:
   1) converting the 6-methoxy-benzothiophene (3) to the corresponding monobromo derivative with N-bromosuccinimide and p-toluenesulfonic acid;
   2) transforming said monobromo derivative into an organomagnesium bromide with Mg under argon in Et$_2$O and then condensing it with 4-methylcyclohexanone in Et$_2$O to afford the corresponding hydroxy substituted methoxybenzothiophene using standard conditions;
   3) treating said hydroxy substituted methoxybenzothiophene with triethylsilane under argon in dichloromethane to afford the corresponding substituted methoxybenzothiophene;
   4) adding the substituted methoxybenzothiophene obtained in step 3) in solution in dichloromethane to a solution of boron tribromide to afford the corresponding hydroxy benzothiophene;
   5) transforming said hydroxy compound into the corresponding sulfamate by treatment with sodium hydride and amidochlorosulfonic acid.

20. Sulfamate benzothiophene derivative according to claim 8 with a melting point of 170° C., said derivative being obtainable by the steps of:
   1) converting the 6-methoxy-benzothiophene (3) to the corresponding monobromo derivative with N-bromosuccinimide and p-toluenesulfonic acid;
   2) transforming said monobromo derivative into an organomagnesium bromide with Mg under argon in Et$_2$O and then condensing it with 4-methylcyclohexanone in Et$_2$O to afford the corresponding hydroxy substituted methoxybenzothiophene using standard conditions;
   3) treating said hydroxy substituted methoxybenzothiophene with triethylsilane under argon in dichloromethane to afford the corresponding substituted methoxybenzothiophene;
   4) adding the substituted methoxybenzothiophene obtained in step 3) in solution in dichloromethane to a solution of boron tribromide to afford the corresponding hydroxy benzothiophene;
   5) transforming said hydroxy compound into the corresponding sulfamate by treatment with sodium hydride and amidochlorosulfonic acid;
   6) oxidizing the resulting compound by 2.2 equivalents of hydrogen peroxide in trifluoroacetic acid and dichloromethane.

21. Sulfamate benzothiophene derivative according to claim 8 with a melting point of 110° C., said derivative being obtainable by the steps of:
1) converting the 6-methoxy-benzothiophene (3) to the corresponding monobromo derivative with N-bromosuccinimide and p-toluenesulfonic acid;
2) transforming said monobromo derivative into an organomagnesium bromide with Mg under argon in $Et_2O$ and then condensing it with 2-methylcyclohexanone in $Et_2O$ to afford the corresponding hydroxy substituted methoxybenzothiophene using standard conditions;
3) treating said hydroxy substituted methoxybenzothiophene with triethylsilane under argon in dichloromethane to afford the corresponding substituted methoxybenzothiophene;
4) adding the substituted methoxybenzothiophene obtained in step 3) in solution in dichloromethane to a solution of boron tribromide to afford the corresponding hydroxy benzothiophene;
5) transforming said hydroxy compound into the corresponding sulfamate by treatment with sodium hydride and amidochlorosulfonic acid.

22. Sulfamate benzothiophene derivative according to claim 8 with a melting point of 92° C., said derivative being obtainable the steps of:
1) converting the 6-methoxy-benzothiophene (3) to the corresponding monobromo derivative with N-bromosuccinimide and p-toluenesulfonic acid;
2) transforming said monobromo derivative into an organomagnesium bromide with Mg under argon in $Et_2O$ and then condensing it with 2-methylcyclohexanone in $Et_2O$ to afford the corresponding hydroxy substituted methoxybenzothiophene using standard conditions;
3) treating said hydroxy substituted methoxybenzothiophene with triethylsilane under argon in dichloromethane to afford the corresponding substituted methoxybenzothiophene;
4) adding the substituted methoxybenzothiophene obtained in step 3) in solution in dichloromethane to a solution of boron tribromide to afford the corresponding hydroxy benzothiophene;
5) transforming said hydroxy compound into the corresponding sulfamate by treatment with sodium hydride and amidochlorosulfonic acid.
6) oxidizing the resulting compound by 2.2 equivalents of hydrogen peroxide in trifluoroacetic acid and dichloromethane.

23. Sulfamate benzothiophene derivative according to claim 8 with a melting point of 72° C., said derivative being obtainable the steps of:
1) converting the 6-methoxy-benzothiophene (3) to the corresponding monobromo derivative with N-bromosuccinimide and p-toluenesulfonic acid;
2) transforming said monobromo derivative into an organomagnesium bromide with Mg under argon in $Et_2O$ and then condensing it with 2,2-dimethylcyclopentanone in $Et_2O$ to afford the corresponding hydroxy substituted methoxybenzothiophene using standard conditions;
3) treating said hydroxy substituted methoxybenzothiophene with triethylsilane under argon in dichloromethane to afford the corresponding substituted methoxybenzothiophene;
4) adding the substituted methoxybenzothiophene obtained in step 3) in solution in dichloromethane to a solution of boron tribromide to afford the corresponding hydroxy benzothiophene;
5) transforming said hydroxy compound into the corresponding sulfamate by treatment with sodium hydride and amidochlorosulfonic acid.

24. Sulfamate benzothiophene derivative according to claim 8 with a melting point of 172° C., said derivative being obtainable by the steps of:
1) converting the 6-methoxy-benzothiophene (3) to the corresponding monobromo derivative with N-bromosuccinimide and p-toluenesulfonic acid;
2) transforming said monobromo derivative into an organomagnesium bromide with Mg under argon in $Et_2O$ and then condensing it with 2,2-dimethylcyclopentanone in $Et_2O$ to afford the corresponding hydroxy substituted methoxybenzothiophene using standard conditions;
3) treating said hydroxy substituted methoxybenzothiophene with triethylsilane under argon in dichloromethane to afford the corresponding substituted methoxybenzothiophene;
4) adding the substituted methoxybenzothiophene obtained in step 3) in solution in dichloromethane to a solution of boron tribromide to afford the corresponding hydroxy benzothiophene;
5) transforming said hydroxy compound into the corresponding sulfamate by treatment with sodium hydride and amidochlorosulfonic acid;
6) oxidizing the resulting compound by 2.2 equivalents of hydrogen peroxide in trifluoroacetic acid and dichloromethane.

25. Sulfamate benzothiophene derivative according to claim 8 with a melting point of 185° C., said derivative being obtainable by the steps of:
1) converting the 6-methoxy-benzothiophene (3) to the corresponding monobromo derivative with N-bromosuccinimide and p-toluenesulfonic acid;
2) transforming said monobromo derivative into an organomagnesium bromide with Mg under argon in $Et_2O$ and then condensing it with 2-adamantanone in $Et_2O$ to afford the corresponding hydroxy substituted methoxybenzothiophene using standard conditions;
3) treating said hydroxy substituted methoxybenzothiophene with triethylsilane under argon in dichloromethane to afford the corresponding substituted methoxybenzothiophene;
4) adding the substituted methoxybenzothiophene obtained in step 3) in solution in dichloromethane to a solution of boron tribromide to afford the corresponding hydroxy benzothiophene;
5) transforming said hydroxy compound into the corresponding sulfamate by treatment with sodium hydride and amidochlorosulfonic acid.

26. Sulfamate benzothiophene derivative according to claim 8 with a melting point of 230° C., said derivative being obtainable by the steps of:
1) converting the 6-methoxy-benzothiophene (3) to the corresponding monobromo derivative with N-bromosuccinimide and p-toluenesulfonic acid;
2) transforming said monobromo derivative into an organomagnesium bromide with Mg under argon in $Et_2O$ and then condensing it with 2-adamantanone in $Et_2O$ to afford the corresponding hydroxy substituted methoxybenzothiophene using standard conditions;
3) treating said hydroxy substituted methoxybenzothiophene with triethylsilane under argon in dichloromethane to afford the corresponding substituted methoxybenzothiophene;
4) adding the substituted methoxybenzothiophene obtained in step 3) in solution in dichloromethane to a solution of boron tribromide to afford the corresponding hydroxy benzothiophene;
5) transforming said hydroxy compound into the corresponding sulfamate by treatment with sodium hydride and amidochlorosulfonic acid;

6) oxidizing the resulting compound by 2.2 equivalents of hydrogen peroxide in trifluoroacetic acid and dichloromethane.

27. Sulfamate benzothiophene derivative according to claim 8 with a melting point of 112° C., said derivative being obtainable by the steps of:
   1) converting the 6-methoxy-benzothiophene (3) to the corresponding monobromo derivative with N-bromosuccinimide and p-toluenesulfonic acid;
   2) transforming said monobromo derivative into an organomagnesium bromide with Mg under argon in $Et_2O$ and then condensing it with propanal in $Et_2O$ to afford the corresponding hydroxy substituted methoxybenzothiophene using standard conditions;
   3) treating said hydroxy substituted methoxybenzothiophene with triethylsilane under argon in dichloromethane to afford the corresponding substituted methoxybenzothiophene;
   4) adding the substituted methoxybenzothiophene obtained in step 3) in solution in dichloromethane to a solution of boron tribromide to afford the corresponding hydroxy benzothiophene;
   5) transforming said hydroxy compound into the corresponding sulfamate by treatment with sodium hydride and amidochlorosulfonic acid.

28. Sulfamate benzothiophene derivative according to claim 8 with a melting point of 159° C., said derivative being obtainable by the steps of:
   1) converting the 6-methoxy-benzothiophene (3) to the corresponding monobromo derivative with N-bromosuccinimide and p-toluenesulfonic acid;
   2) transforming said monobromo derivative into an organomagnesium bromide with Mg under argon in $Et_2O$ and then condensing it with propanal in $Et_2O$ to afford the corresponding hydroxy substituted methoxybenzothiophene using standard conditions;
   3) treating said hydroxy substituted methoxybenzothiophene with triethylsilane under argon in dichloromethane to afford the corresponding substituted methoxybenzothiophene;
   4) adding the substituted methoxybenzothiophene obtained in step 3) in solution in dichloromethane to a solution of boron tribromide to afford the corresponding hydroxy benzothiophene;
   5) transforming said hydroxy compound into the corresponding sulfamate by treatment with sodium hydride and amidochlorosulfonic acid;
   6) oxidizing the resulting compound by 2.2 equivalents of hydrogen peroxide in trifluoroacetic acid and dichloromethane.

29. Sulfamate benzothiophene derivative according to claim 8 with a melting point of 125° C., said derivative being obtainable by the steps of:
   1) converting the 6-methoxy-benzothiophene (3) to the corresponding monobromo derivative with N-bromosuccinimide and p-toluenesulfonic acid;
   2) transforming said monobromo derivative into an organomagnesium bromide with Mg under argon in $Et_2O$ and then condensing it with hexanal in $Et_2O$ to afford the corresponding hydroxy substituted methoxybenzothiophene using standard conditions;
   3) treating said hydroxy substituted methoxybenzothiophene with triethylsilane under argon in dichloromethane to afford the corresponding substituted methoxybenzothiophene;
   4) adding the substituted methoxybenzothiophene obtained in step 3) in solution in dichloromethane to a solution of boron tribromide to afford the corresponding hydroxy benzothiophene;
   5) transforming said hydroxy compound into the corresponding sulfamate by treatment with sodium hydride and amidochlorosulfonic acid.

30. Sulfamate benzothiophene derivative according to claim 8 with a melting point of 98° C., said derivative being obtainable by the steps of:
   1) converting the 6-methoxy-benzothiophene (3) to the corresponding monobromo derivative with N-bromosuccinimide and p-toluenesulfonic acid;
   2) transforming said monobromo derivative into an organomagnesium bromide with Mg under argon in $Et_2O$ and then condensing it with hexanal in $Et_2O$ to afford the corresponding hydroxy substituted methoxybenzothiophene using standard conditions;
   3) treating said hydroxy substituted methoxybenzothiophene with triethylsilane under argon in dichloromethane to afford the corresponding substituted methoxybenzothiophene;
   4) adding the substituted methoxybenzothiophene obtained in step 3) in solution in dichloromethane to a solution of boron tribromide to afford the corresponding hydroxy benzothiophene;
   5) transforming said hydroxy compound into the corresponding sulfamate by treatment with sodium hydride and amidochlorosulfonic acid;
   6) oxidizing the resulting compound by 2.2 equivalents of hydrogen peroxide in trifluoroacetic acid and dichloromethane.

31. Sulfamate benzothiophene derivative according to claim 8 with a melting point of 115° C., said derivative being obtainable by the steps of:
   1) converting the 6-methoxy-benzothiophene (3) to the corresponding monobromo derivative with N-bromosuccinimide and p-toluenesulfonic acid;
   2) transforming said monobromo derivative into an organomagnesium bromide with Mg under argon in $Et_2O$ and then condensing it with cyclohexanecarboxaldehyde in $Et_2O$ to afford the corresponding hydroxy substituted methoxybenzothiophene using standard conditions;
   3) treating said hydroxy substituted methoxybenzothiophene with triethylsilane under argon in dichloromethane to afford the corresponding substituted benzothiophene;
   4) adding the substituted methoxybenzothiophene obtained in step 3) in solution in dichloromethane to a solution of boron tribromide to afford the corresponding hydroxy benzothiophene;
   5) transforming said hydroxy compound into the corresponding sulfamate by treatment with sodium hydride and amidochlorosulfonic acid.

32. Sulfamate benzothiophene derivative according to claim 8 with a melting point of 132° C., said derivative being obtainable by the steps of:
   1) converting the 6-methoxy-benzothiophene (3) to the corresponding monobromo derivative with N-bromosuccinimide and p-toluenesulfonic acid;
   2) transforming said monobromo derivative into an organomagnesium bromide with Mg under argon in $Et_2O$ and then condensing it with cyclohexanecarboxaldehyde in $Et_2O$ to afford the corresponding hydroxy substituted methoxybenzothiophene using standard conditions;
   3) treating said hydroxy substituted methoxybenzothiophene with triethylsilane under argon in dichloromethane to afford the corresponding substituted benzothiophene;

4) adding the substituted methoxybenzothiophene obtained in step 3) in solution in dichloromethane to a solution of boron tribromide to afford the corresponding hydroxy benzothiophene;
5) transforming said hydroxy compound into the corresponding sulfamate by treatment with sodium hydride and amidochlorosulfonic acid;
6) oxidizing the resulting compound by 2.2 equivalents of hydrogen peroxide in trifluoroacetic acid and dichloromethane.

33. Sulfamate benzothiophene derivative according to claim 8 with a melting point of 90° C., said derivative being obtainable by the steps of:
1) converting the 6-methoxy-benzothiophene (3) to the corresponding monobromo derivative with N-bromosuccinimide and p-toluenesulfonic acid;
2) transforming said monobromo derivative into an organomagnesium bromide with Mg under argon in $Et_2O$ and then condensing it with cycloheptanecarboxaldehyde in $Et_2O$ to afford the corresponding hydroxy substituted methoxybenzothiophene using standard conditions;
3) treating said hydroxy substituted methoxybenzothiophene with triethylsilane under argon in dichloromethane to afford the corresponding substituted methoxybenzothiophene;
4) adding the substituted methoxybenzothiophene obtained in step 3) in solution in dichloromethane to a solution of boron tribromide to afford the corresponding hydroxy benzothiophene;
5) transforming said hydroxy compound into the corresponding sulfamate by treatment with sodium hydride and amidochlorosulfonic acid.

34. Sulfamate benzothiophene derivative according to claim 8 with a melting point of 135° C., said derivative being obtainable by the steps of:
1) converting the 6-methoxy-benzothiophene (3) to the corresponding monobromo derivative with N-bromosuccinimide and p-toluenesulfonic acid;
2) transforming said monobromo derivative into an organomagnesium bromide with Mg under argon in $Et_2O$ and then condensing it with cycloheptanecarboxaldehyde in $Et_2O$ to afford the corresponding hydroxy substituted methoxybenzothiophene using standard conditions;
3) treating said hydroxy substituted methoxybenzothiophene with triethylsilane under argon in dichloromethane to afford the corresponding substituted methoxybenzothiophene;
4) adding the substituted methoxybenzothiophene obtained in step 3) in solution in dichloromethane to a solution of boron tribromide to afford the corresponding hydroxy benzothiophene;
5) transforming said hydroxy compound into the corresponding sulfamate by treatment with sodium hydride and amidochlorosulfonic acid;
6) oxidizing the resulting compound by 2.2 equivalents of hydrogen peroxide in trifluoroacetic acid and dichloromethane.

35. Sulfamate benzothiophene derivative according to claim 8 with a melting point of 107° C., said derivative being obtainable by the steps of:
1) converting the 6-methoxy-benzothiophene (3) to the corresponding monobromo derivative with N-bromosuccinimide and p-toluenesulfonic acid;
2) transforming said monobromo derivative into an organomagnesium bromide with Mg under argon in $Et_2O$ and then condensing it with cycloheptanone in $Et_2O$ to afford the corresponding hydroxy substituted methoxybenzothiophene using standard conditions;
3) treating said hydroxy substituted methoxybenzothiophene with triethylsilane under argon in dichloromethane to afford the corresponding substituted methoxybenzothiophene;
4) alkylating the corresponding substituted methoxybenzothiophene by adding iodomethane to a mixture of said monosubstituted methoxybenzothiophene in a solution of n-butyl lithium in hexane to afford the corresponding methoxybenzothiophene;
5) adding the substituted methoxybenzothiophene obtained in step 4) in solution in dichloromethane to a solution of boron tribromide to afford the corresponding hydroxy benzothiophene;
6) transforming said hydroxy compound into the corresponding sulfamate by treatment with sodium hydride and amidochlorosulfonic acid.

36. Sulfamate benzothiophene derivative according to claim 8 with a melting point of 90° C., said derivative being obtainable by the steps of:
1) converting the 6-methoxy-benzothiophene (3) to the corresponding monobromo derivative with N-bromosuccinimide and p-toluenesulfonic acid;
2) transforming said monobromo derivative into an organomagnesium bromide with Mg under argon in $Et_2O$ and then condensing it with cycloheptanone in $Et_2O$ to afford the corresponding hydroxy substituted methoxybenzothiophene using standard conditions;
3) treating said hydroxy substituted methoxybenzothiophene with triethylsilane under argon in dichloromethane to afford the corresponding substituted methoxybenzothiophene;
4) alkylating the corresponding substituted methoxybenzothiophene by adding iodomethane to a mixture of said monosubstituted methoxybenzothiophene in a solution of n-butyl lithium in hexane to afford the corresponding methoxybenzothiophene;
5) adding the substituted methoxybenzothiophene obtained in step 4) in solution in dichloromethane to a solution of boron tribromide to afford the corresponding hydroxy benzothiophene;
6) transforming said hydroxy compound into the corresponding sulfamate by treatment with sodium hydride and amidochlorosulfonic acid;
7) oxidizing the resulting compound by 2.2 equivalents of hydrogen peroxide in trifluoroacetic acid and dichloromethane.

37. Sulfamate benzothiophene derivative according to claim 8 in the form of a lipid oil, said derivative being obtainable by the steps of:
1) converting the 6-methoxy-benzothiophene (3) to the corresponding monobromo derivative with N-bromosuccinimide and p-toluenesulfonic acid;
2) transforming said monobromo derivative into an organomagnesium bromide with Mg under argon in $Et_2O$ and then condensing it with cycloheptanone in $Et_2O$ to afford the corresponding hydroxy substituted methoxybenzothiophene using standard conditions;
3) treating said hydroxy substituted methoxybenzothiophene with triethylsilane under argon in dichloromethane to afford the corresponding substituted methoxybenzothiophene;
4) alkylating the corresponding substituted methoxybenzothiophene by adding bromobutane to a mixture of said monosubstituted methoxybenzothiophene in a solution of n-butyl lithium in hexane to afford the corresponding methoxybenzothiophene;
5) adding the substituted methoxybenzothiophene obtained in step 4) in solution in dichloromethane to a solution of boron tribromide to afford the corresponding hydroxy benzothiophene;
6) transforming said hydroxy compound into the corresponding sulfamate by treatment with sodium hydride and amidochlorosulfonic acid.

38. Sulfamate benzothiophene derivative according to claim 8 under the form of a limpid oil, said derivative being obtainable by the steps of:
1) converting the 6-methoxy-benzothiophene (3) to the corresponding monobromo derivative with N-bromo-succinimide and p-toluenesulfonic acid;
2) transforming said monobromo derivative into an organomagnesium bromide with Mg under argon in Et$_2$O and then condensing it with cycloheptanone in Et$_2$O to afford the corresponding hydroxy substituted methoxybenzothiophene using standard conditions;
3) treating said hydroxy substituted methoxybenzothiophene with triethylsilane under argon in dichloromethane to afford the corresponding substituted methoxybenzothiophene;
4) alkylating the corresponding substituted methoxybenzothiophene by adding bromobutane to a mixture of said monosubstituted methoxybenzothiophene in a solution of n-butyl lithium in hexane to afford the corresponding methoxybenzothiophene;
5) adding the substituted methoxybenzothiophene obtained in step 4) in solution in dichloromethane to a solution of boron tribromide to afford the corresponding hydroxy benzothiophene;
6) transforming said hydroxy compound into the corresponding sulfamate by treatment with sodium hydride and amidochlorosulfonic acid;
7) oxidizing the resulting compound by 2.2 equivalents of hydrogen peroxide in trifluoroacetic acid and dichloromethane.

39. Sulfamate benzothiophene derivative according to claim 8 with a melting point of 110° C., said derivative being obtainable by the steps of:
1) converting the 6-methoxy-benzothiophene (3) to the corresponding monobromo derivative with N-bromo-succinimide and p-toluenesulfonic acid;
2) transforming said monobromo derivative into an organomagnesium bromide with Mg under argon in Et$_2$O and then condensing it with cyclopentanone in Et$_2$O to afford the corresponding hydroxy substituted methoxybenzothiophene using standard conditions;
3) treating said hydroxy substituted methoxybenzothiophene with triethylsilane under argon in dichloromethane to afford the corresponding substituted methoxybenzothiophene;
4) adding the substituted methoxybenzothiophene obtained in step 3) in solution in dichloromethane to a solution of boron tribromide to afford the corresponding hydroxy benzothiophene;
5) transforming said hydroxy compound into the corresponding sulfamate by treatment with sodium hydride and amidochlorosulfonic acid.

40. A compound of formula (I):

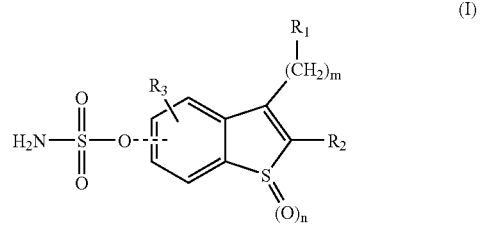

wherein:
R$_1$ is hydrogen;
R$_2$ is hydrogen, a (C$_1$-C$_6$)alkyl or a (C$_3$-C$_{12}$)cycloalkyl;
R$_3$ is hydrogen, a (C$_1$-C$_6$)alkoxy or a halogen;
m is 0;
n is 0, 1, 2;
the dotted line indicates that the sulfamate group is in position 5- or 6- of the benzothiophene ring.

41. A compound of formula (I):

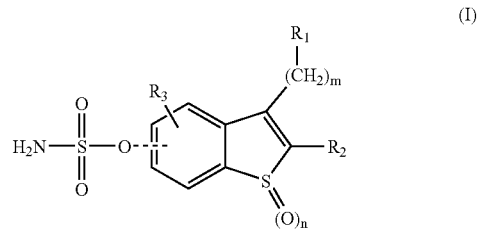

wherein:
R$_1$ and R$_2$ form together a group —(CH$_2$)$_p$- in which p is 3, 4 or 5;
R$_3$ is hydrogen, a (C$_1$-C$_6$)alkoxy or a halogen;
4. n is 0, 1, 2;
5. m is 0;
6. the dotted line indicates that the sulfamate group is in position 5- or 6- of the benzothiophene ring.

42. The compound according to claim 40, wherein R$_3$ is hydrogen.

43. The compound according to claim 40, wherein the sulfamate group is in position 6- of the benzothiophene ring.

44. The compound according to claim 41, which is the sulfamic acid, 1,2,3,4-tetrahydro-dibenzothiophene-7-yl ester.

45. The compound according to claim 41, which is the sulfamic acid, 1,2,3,4-tetrahydro-dibenzothiophene-7-yl-1,1-dioxide ester.

46. A pharmaceutical composition comprising a compound according to claim 1, and a pharmaceutically acceptable carrier.

47. The compound according to claim 1, which is sulfamic acid, 2-hexyl-benzothiophene-6-yl-1,1-dioxide ester, sulfamic acid, 2-cyclohexylmethyl-benzothiophene-6-yl-1,1-dioxide ester or sulfamic acid, 2-cycloheptylmethyl-benzothiophene-6-yl-1,1-dioxide ester.

* * * * *